(12) United States Patent
Farin et al.

(10) Patent No.: US 10,390,694 B2
(45) Date of Patent: Aug. 27, 2019

(54) MICRO LAPAROSCOPY DEVICES AND DEPLOYMENTS THEREOF

(75) Inventors: Danny Farin, Hod-Hasharon (IL); Yehuda Bachar, Givat-Shmuel (IL); Ronny Winshtein, Ramat-Hasharon (IL)

(73) Assignee: EON SURGICAL, LTD., Tel Aviv (IL)

( * ) Notice: Subject to any disclaimer, the term of this patent is extended or adjusted under 35 U.S.C. 154(b) by 134 days.

(21) Appl. No.: 13/824,814

(22) PCT Filed: Sep. 19, 2011

(86) PCT No.: PCT/IB2011/054102
§ 371 (c)(1),
(2), (4) Date: Sep. 5, 2013

(87) PCT Pub. No.: WO2012/035524
PCT Pub. Date: Mar. 22, 2012

(65) Prior Publication Data
US 2014/0005474 A1    Jan. 2, 2014

Related U.S. Application Data

(60) Provisional application No. 61/384,288, filed on Sep. 19, 2010, provisional application No. 61/493,423, filed on Jun. 4, 2011.

(51) Int. Cl.
*A61B 1/313* (2006.01)
*A61B 1/00* (2006.01)
(Continued)

(52) U.S. Cl.
CPC ........ *A61B 1/3132* (2013.01); *A61B 1/00087* (2013.01); *A61B 1/00154* (2013.01);
(Continued)

(58) Field of Classification Search
CPC ............ A61B 17/3421; A61B 17/3423; A61B 17/3431; A61B 17/3439; A61B 17/00234;
(Continued)

(56) References Cited

U.S. PATENT DOCUMENTS 4,177,814 A    12/1979    Knepshield et al.
4,424,833 A    1/1984    Spector et al.
(Continued)

FOREIGN PATENT DOCUMENTS

CN    1610568 A    4/2005
CN    1764410 A    4/2006
(Continued)

OTHER PUBLICATIONS

International Search Report from International Application No. PCT/IB2011/054102 dated Jun. 13, 2012.
(Continued)

*Primary Examiner* — Eric S Gibson
*Assistant Examiner* — Marcela I Shirsat
(74) *Attorney, Agent, or Firm* — Baker & Hostetler LLP

(57) ABSTRACT

An apparatus for reversely deactivating a port seal in a laparoscopic port and providing a continuous passage between the laparoscopic port and a remote location in a body cavity.

19 Claims, 16 Drawing Sheets

(51) Int. Cl.
*A61B 17/00* (2006.01)
*A61B 17/04* (2006.01)
*A61B 17/34* (2006.01)
*A61B 1/05* (2006.01)
*A61B 1/32* (2006.01)
*A61B 17/02* (2006.01)
*A61B 17/22* (2006.01)
*A61B 17/06* (2006.01)
*A61B 17/221* (2006.01)
*A61B 34/30* (2016.01)
*A61B 90/00* (2016.01)

(52) U.S. Cl.
CPC ........ *A61B 1/053* (2013.01); *A61B 1/32* (2013.01); *A61B 17/00234* (2013.01); *A61B 17/0218* (2013.01); *A61B 17/0485* (2013.01); *A61B 17/3421* (2013.01); *A61B 17/22031* (2013.01); *A61B 17/3439* (2013.01); *A61B 17/3478* (2013.01); *A61B 90/361* (2016.02); *A61B 2017/00473* (2013.01); *A61B 2017/00867* (2013.01); *A61B 2017/06104* (2013.01); *A61B 2017/2212* (2013.01); *A61B 2017/22035* (2013.01); *A61B 2017/3405* (2013.01); *A61B 2017/3443* (2013.01); *A61B 2034/302* (2016.02); *A61B 2090/034* (2016.02)

(58) Field of Classification Search
CPC ... A61B 2017/3425; A61B 2017/3443; A61M 39/04; A61M 39/06; A61M 39/0613; A61M 39/0693; A61M 2039/042; A61M 2039/0626; A61M 2039/0633; A61M 2039/064; A61M 2039/0646; A61M 2039/0653; A61M 2039/066; A61M 2039/0666; A61M 2039/0673
USPC ............. 600/104, 204, 205, 206, 208, 215
See application file for complete search history.

(56) References Cited

U.S. PATENT DOCUMENTS

| | | |
|---|---|---|
| 4,453,928 A | 6/1984 | Steiger |
| 4,655,752 A | 4/1987 | Honkanen et al. |
| 4,746,975 A | 5/1988 | Ogiu |
| 4,831,444 A | 5/1989 | Kato |
| 4,929,235 A | 5/1990 | Merry et al. |
| 4,943,280 A | 7/1990 | Lander |
| 4,944,732 A | 7/1990 | Russo |
| 4,960,412 A | 10/1990 | Fink |
| 4,978,341 A | 12/1990 | Niederhauser |
| 5,015,250 A | 5/1991 | Foster |
| 5,092,846 A | 3/1992 | Nishijima et al. |
| 5,112,310 A | 5/1992 | Grobe |
| 5,127,626 A | 7/1992 | Hilal |
| 5,152,749 A | 10/1992 | Giesy et al. |
| 5,167,627 A | 12/1992 | Clegg et al. |
| 5,167,644 A * | 12/1992 | Fischell ............... A61M 39/20 604/264 |
| 5,180,373 A | 1/1993 | Green et al. |
| 5,197,955 A | 3/1993 | Stephens et al. |
| 5,209,736 A | 5/1993 | Stephens et al. |
| 5,211,370 A | 5/1993 | Powers |
| 5,226,891 A | 7/1993 | Bushatz et al. |
| 5,242,412 A | 9/1993 | Blake, III |
| 5,295,994 A | 3/1994 | Bonutti |
| 5,300,035 A * | 4/1994 | Clement ........... A61M 39/0613 604/167.01 |
| 5,308,336 A | 5/1994 | Hart et al. |
| 5,309,895 A | 5/1994 | Yabe |
| 5,312,363 A | 5/1994 | Ryan et al. |
| 5,330,437 A | 7/1994 | Durman |
| 5,342,315 A | 8/1994 | Rowe et al. |
| 5,352,219 A | 10/1994 | Reddy |
| 5,375,588 A | 12/1994 | Yoon |
| 5,376,077 A | 12/1994 | Gomringer |
| 5,389,077 A | 2/1995 | Melinyshyn et al. |
| 5,395,342 A | 3/1995 | Yoon |
| 5,401,248 A | 3/1995 | Bencini |
| 5,441,059 A | 8/1995 | Dannan |
| 5,476,475 A | 12/1995 | Gadberry |
| 5,511,564 A | 4/1996 | Wilk |
| 5,545,179 A | 8/1996 | Williamson, IV |
| 5,569,183 A | 10/1996 | Kieturakis |
| 5,593,402 A | 1/1997 | Patrick |
| 5,634,911 A | 6/1997 | Hermann et al. |
| 5,645,549 A | 7/1997 | Boyd et al. |
| 5,658,306 A | 8/1997 | Kieturakis et al. |
| 5,707,359 A | 1/1998 | Bufalini |
| 5,720,761 A | 2/1998 | Kaali |
| 5,755,713 A | 5/1998 | Bilof et al. |
| 5,792,113 A | 8/1998 | Kramer et al. |
| 5,827,228 A | 10/1998 | Rowe |
| 5,871,474 A | 2/1999 | Hermann et al. |
| 5,882,344 A | 3/1999 | Stouder, Jr. et al. |
| 5,895,377 A | 4/1999 | Smith et al. |
| 5,896,166 A | 4/1999 | D'Alfonso et al. |
| 5,976,146 A | 11/1999 | Ogawa et al. |
| 5,979,452 A | 11/1999 | Fogarty et al. |
| 5,980,455 A | 11/1999 | Daniel et al. |
| 5,989,240 A | 11/1999 | Strowe |
| 6,004,303 A | 12/1999 | Peterson |
| 6,095,970 A | 8/2000 | Hidaka et al. |
| 6,106,511 A | 8/2000 | Jensen |
| 6,120,511 A | 9/2000 | Chan |
| 6,146,402 A | 11/2000 | Munoz |
| 6,149,642 A | 11/2000 | Gerhart et al. |
| 6,159,200 A | 12/2000 | Verdura et al. |
| 6,165,184 A | 12/2000 | Verdura et al. |
| 6,187,000 B1 | 2/2001 | Davison et al. |
| 6,197,002 B1 * | 3/2001 | Peterson ............... 604/164.01 |
| 6,258,065 B1 | 7/2001 | Dennis et al. |
| 6,287,280 B1 | 9/2001 | Lampropoulos et al. |
| 6,309,345 B1 | 10/2001 | Stelzer et al. |
| 6,309,397 B1 | 10/2001 | Julian et al. |
| 6,312,435 B1 | 11/2001 | Wallace et al. |
| 6,312,443 B1 * | 11/2001 | Stone ............... A61B 17/025 606/198 |
| 6,436,107 B1 | 8/2002 | Wang et al. |
| 6,443,159 B1 | 9/2002 | Fogarty et al. |
| 6,447,489 B1 | 9/2002 | Peterson |
| 6,569,120 B1 | 5/2003 | Green et al. |
| 6,602,240 B2 | 8/2003 | Hermann et al. |
| 6,608,639 B2 | 8/2003 | McGovern |
| 6,645,196 B1 | 11/2003 | Nixon et al. |
| 6,752,827 B2 | 6/2004 | Ross et al. |
| 6,802,836 B2 | 10/2004 | Bouphavichith et al. |
| 6,860,869 B2 | 3/2005 | Dennis |
| 6,918,871 B2 | 7/2005 | Schulze |
| 6,963,792 B1 | 11/2005 | Green |
| 7,018,384 B2 | 3/2006 | Skakoon |
| 7,041,083 B2 | 5/2006 | Chu et al. |
| 7,044,937 B1 | 5/2006 | Kirwan et al. |
| 7,056,303 B2 | 6/2006 | Dennis et al. |
| 7,083,626 B2 | 8/2006 | Brustad et al. |
| 7,125,403 B2 | 10/2006 | Julian et al. |
| 7,163,525 B2 | 1/2007 | Franer |
| 7,226,411 B2 | 6/2007 | Akiba |
| 7,235,062 B2 | 6/2007 | Brustad |
| 7,297,141 B2 | 11/2007 | Kathrani et al. |
| 7,300,397 B2 | 11/2007 | Adler et al. |
| 7,331,967 B2 | 2/2008 | Lee et al. |
| 7,341,587 B2 | 3/2008 | Molz, IV et al. |
| 7,367,973 B2 | 5/2008 | Manzo et al. |
| 7,371,227 B2 | 5/2008 | Zeiner |
| 7,390,317 B2 | 6/2008 | Taylor et al. |
| 7,438,702 B2 | 10/2008 | Hart et al. |
| 7,473,221 B2 | 1/2009 | Ewers et al. |
| 7,481,765 B2 | 1/2009 | Ewers et al. |
| 7,494,460 B2 | 2/2009 | Haarstad et al. |
| 7,559,887 B2 | 7/2009 | Dannan |
| 7,563,250 B2 | 7/2009 | Wenchell |

(56) References Cited

U.S. PATENT DOCUMENTS

| | | |
|---|---|---|
| 7,641,648 B2 | 1/2010 | Bouphavichith et al. |
| 7,651,478 B2 | 1/2010 | Brustad |
| 7,691,103 B2 | 4/2010 | Fernandez et al. |
| 7,717,878 B2 | 5/2010 | Smith |
| 7,722,599 B2 | 5/2010 | Julian et al. |
| 7,753,901 B2 | 7/2010 | Piskun et al. |
| 7,753,928 B2 | 7/2010 | Torre et al. |
| 7,779,716 B2 | 8/2010 | Dellach et al. |
| 7,803,135 B2 | 9/2010 | Franer |
| 7,828,808 B2 | 11/2010 | Hinman et al. |
| 7,833,275 B2 | 11/2010 | Mears et al. |
| 7,758,569 B2 | 12/2010 | Brock |
| 7,857,754 B2 | 12/2010 | Spivey et al. |
| 7,862,553 B2 | 1/2011 | Ewaschuk |
| 7,883,493 B2 | 2/2011 | Brustad |
| 7,918,376 B1 | 4/2011 | Knodel et al. |
| 7,918,826 B2 | 4/2011 | Armstrong et al. |
| 7,918,827 B2 | 4/2011 | Smith |
| 7,935,130 B2 | 5/2011 | Williams |
| 7,972,307 B2 | 7/2011 | Kraus et al. |
| 7,976,501 B2 | 7/2011 | Franer et al. |
| 7,988,671 B2 | 8/2011 | Albrecht et al. |
| 8,002,764 B2 | 8/2011 | High |
| 8,007,472 B2 | 8/2011 | Exline et al. |
| 8,007,492 B2 | 8/2011 | Dipoto et al. |
| 8,012,160 B2 | 9/2011 | Jensen et al. |
| 8,016,755 B2 | 9/2011 | Ewers et al. |
| 8,021,358 B2 | 9/2011 | Doyle et al. |
| 8,029,475 B2 | 10/2011 | Franer et al. |
| 8,033,995 B2 | 10/2011 | Cropper et al. |
| 8,070,676 B2 | 12/2011 | Ewers et al. |
| 8,075,477 B2 | 12/2011 | Nakamura et al. |
| 8,075,530 B2 | 12/2011 | Taylor et al. |
| 8,088,062 B2 | 1/2012 | Zwolinski |
| 8,097,000 B2 | 1/2012 | Albrecht |
| 8,100,929 B2 | 1/2012 | Franer et al. |
| 8,105,234 B2 | 1/2012 | Ewers et al. |
| 8,109,910 B2 | 2/2012 | Zastawny et al. |
| 8,133,254 B2 | 3/2012 | Dumbauld et al. |
| 8,137,267 B2 * | 3/2012 | Shelton et al. ............... 600/203 |
| 8,147,457 B2 | 4/2012 | Michael et al. |
| 8,152,773 B2 | 4/2012 | Albrecht et al. |
| 8,152,774 B2 | 4/2012 | Pasqualucci |
| 8,172,806 B2 | 5/2012 | Smith |
| 8,192,405 B2 | 6/2012 | Racenet et al. |
| 8,226,798 B2 | 7/2012 | Baldwin et al. |
| 8,348,828 B2 | 1/2013 | Asada et al. |
| 8,353,487 B2 | 1/2013 | Trusty et al. |
| 8,353,897 B2 | 1/2013 | Doyle et al. |
| 8,376,938 B2 | 2/2013 | Morgan et al. |
| 8,377,044 B2 | 2/2013 | Coe et al. |
| 8,409,172 B2 | 4/2013 | Moll et al. |
| 8,423,182 B2 | 4/2013 | Robinson et al. |
| 8,425,406 B2 | 4/2013 | Smith et al. |
| 8,430,851 B2 | 4/2013 | McGinley et al. |
| 8,444,631 B2 | 5/2013 | Yeung et al. |
| 8,458,896 B2 | 6/2013 | Chandrasekaran et al. |
| 8,506,555 B2 | 8/2013 | Morales |
| 8,852,253 B2 * | 10/2014 | Mafi ............................ 606/323 |
| 9,549,719 B2 | 1/2017 | Shohat et al. |
| 2002/0095144 A1 | 7/2002 | Carl |
| 2003/0004529 A1 | 1/2003 | Tsonton et al. |
| 2003/0041865 A1 | 3/2003 | Mollenauer |
| 2003/0060687 A1 | 3/2003 | Kleeman et al. |
| 2003/0130693 A1 | 7/2003 | Levin et al. |
| 2004/0068232 A1 | 4/2004 | Hart et al. |
| 2004/0181150 A1 | 9/2004 | Evans et al. |
| 2004/0260246 A1 | 12/2004 | Desmond |
| 2005/0004512 A1 | 1/2005 | Campbell et al. |
| 2005/0015103 A1 | 1/2005 | Popov |
| 2005/0096507 A1 | 5/2005 | Prosek |
| 2005/0131349 A1 | 6/2005 | Albrecht et al. |
| 2005/0203543 A1 | 9/2005 | Hilal et al. |
| 2005/0234294 A1 | 10/2005 | Saadat et al. |
| 2006/0200184 A1 | 9/2006 | Deal |
| 2006/0200185 A1 | 9/2006 | Marchek et al. |
| 2006/0276835 A1 | 12/2006 | Uchida |
| 2007/0027447 A1 | 2/2007 | Theroux et al. |
| 2007/0073323 A1 | 3/2007 | Carter et al. |
| 2007/0078463 A1 | 4/2007 | Malandain |
| 2007/0296827 A1 | 5/2007 | Kubota et al. |
| 2007/0179507 A1 | 8/2007 | Shah |
| 2007/0182842 A1 | 8/2007 | Sonnenschein et al. |
| 2007/0255257 A1 | 11/2007 | Willis et al. |
| 2008/0183153 A1 | 7/2008 | Enns |
| 2008/0228213 A1 | 9/2008 | Blakeney et al. |
| 2008/0242939 A1 | 10/2008 | Johnston |
| 2008/0249475 A1 | 10/2008 | Albrecht et al. |
| 2008/0249558 A1 * | 10/2008 | Cahill ............... A61B 17/3439 606/198 |
| 2008/0262302 A1 | 10/2008 | Azarbarzin et al. |
| 2008/0287926 A1 | 11/2008 | Kheir |
| 2008/0309758 A1 | 12/2008 | Karasawa et al. |
| 2009/0024163 A1 | 1/2009 | Zeiner et al. |
| 2009/0082627 A1 | 3/2009 | Karasawa et al. |
| 2009/0082634 A1 | 3/2009 | Kathrani et al. |
| 2009/0131754 A1 | 5/2009 | Ewers et al. |
| 2009/0192344 A1 | 7/2009 | Bakos et al. |
| 2009/0209947 A1 | 8/2009 | Gordin et al. |
| 2009/0254050 A1 | 10/2009 | Bottcher |
| 2009/0259141 A1 | 10/2009 | Ewers et al. |
| 2009/0259175 A1 | 10/2009 | Nordgren |
| 2009/0259184 A1 * | 10/2009 | Okoniewski ............. 604/165.02 |
| 2009/0270676 A1 | 10/2009 | Sisvol |
| 2009/0270679 A1 | 10/2009 | Hoge et al. |
| 2009/0270685 A1 | 10/2009 | Moreno et al. |
| 2009/0270818 A1 | 10/2009 | Duke |
| 2009/0287045 A1 | 11/2009 | Mitelberg et al. |
| 2009/0299135 A1 | 12/2009 | Spivey |
| 2010/0010501 A2 | 1/2010 | Meade et al. |
| 2010/0057110 A1 | 3/2010 | Lampropoulos et al. |
| 2010/0063437 A1 | 3/2010 | Nelson et al. |
| 2010/0076259 A1 | 3/2010 | Asada et al. |
| 2010/0081883 A1 | 4/2010 | Murray et al. |
| 2010/0125164 A1 | 5/2010 | LaBombard |
| 2010/0191050 A1 | 7/2010 | Zwolinski |
| 2010/0191255 A1 | 7/2010 | Crainich et al. |
| 2010/0241136 A1 | 9/2010 | Doyle et al. |
| 2010/0249700 A1 | 9/2010 | Spivey |
| 2010/0268028 A1 | 10/2010 | Ghabrial |
| 2010/0280326 A1 | 11/2010 | Hess et al. |
| 2010/0324369 A1 * | 12/2010 | Smith ............... A61B 1/00087 600/138 |
| 2010/0331856 A1 | 12/2010 | Carlson et al. |
| 2011/0028794 A1 | 2/2011 | Widenhouse et al. |
| 2011/0066000 A1 | 3/2011 | Ibrahim et al. |
| 2011/0077460 A1 | 3/2011 | Hashiba et al. |
| 2011/0087266 A1 | 4/2011 | Conlon et al. |
| 2011/0124960 A1 | 5/2011 | St. Onge et al. |
| 2011/0124961 A1 | 5/2011 | Zimmon |
| 2011/0130787 A1 | 6/2011 | Cinquin et al. |
| 2011/0152615 A1 | 6/2011 | Schostek et al. |
| 2011/0230723 A1 | 9/2011 | Castro et al. |
| 2011/0237890 A1 | 9/2011 | Farritor et al. |
| 2011/0276038 A1 | 11/2011 | McIntyre et al. |
| 2011/0277775 A1 | 11/2011 | Holop et al. |
| 2011/0288573 A1 | 11/2011 | Yates et al. |
| 2011/0290854 A1 | 12/2011 | Timm et al. |
| 2012/0083826 A1 | 4/2012 | Chao et al. |

FOREIGN PATENT DOCUMENTS

| | | |
|---|---|---|
| CN | 101478923 A | 7/2009 |
| EP | 1515665 B1 | 2/2012 |
| JP | 2007-534380 A | 11/2007 |
| WO | WO1993008867 A3 | 6/1993 |
| WO | 1994007552 A1 | 4/1994 |
| WO | WO1994013335 A1 | 6/1994 |
| WO | WO199422382 A1 | 10/1994 |
| WO | 199426179 A1 | 11/1994 |
| WO | WO1995022298 A1 | 8/1995 |
| WO | WO199530374 A1 | 11/1995 |
| WO | WO1996032889 A1 | 10/1996 |
| WO | 1996040016 A3 | 10/1998 |

(56) References Cited

FOREIGN PATENT DOCUMENTS

| | | |
|---|---|---|
| WO | WO1998053865 A1 | 12/1998 |
| WO | 199935971 A1 | 7/1999 |
| WO | 02/07618 A1 | 1/2002 |
| WO | 03/015848 A1 | 2/2003 |
| WO | WO2003013367 A3 | 7/2003 |
| WO | WO2003059412 A3 | 11/2003 |
| WO | WO2004043267 A3 | 9/2004 |
| WO | 2005-122921 A2 | 12/2005 |
| WO | WO200586564 A3 | 3/2006 |
| WO | WO2005112799 A8 | 8/2006 |
| WO | WO2006118650 A1 | 11/2006 |
| WO | WO2004066828 A3 | 12/2006 |
| WO | 07/08332 A2 | 1/2007 |
| WO | 07/073931 A1 | 7/2007 |
| WO | WO2007088206 A3 | 9/2007 |
| WO | 20100114634 A1 | 10/2007 |
| WO | WO2007111571 A1 | 10/2007 |
| WO | WO2007136829 A1 | 11/2007 |
| WO | 2007119060 A3 | 12/2007 |
| WO | WO2008005433 A1 | 1/2008 |
| WO | WO2008029109 A1 | 3/2008 |
| WO | WO2008057117 A1 | 5/2008 |
| WO | WO2008045744 A3 | 7/2008 |
| WO | WO2008121259 A3 | 12/2008 |
| WO | 2009147669 A1 | 12/2009 |
| WO | 2010098871 A3 | 2/2010 |
| WO | 10/440051 A1 | 4/2010 |
| WO | 2010/042913 A2 | 4/2010 |
| WO | 2010/060436 A1 | 6/2010 |
| WO | WO2010081482 A1 | 7/2010 |
| WO | 2010111319 A1 | 9/2010 |
| WO | WO2010114634 A1 | 10/2010 |
| WO | WO2010136805 A1 | 12/2010 |
| WO | WO2011056458 A1 | 5/2011 |
| WO | 2011140444 A1 | 11/2011 |
| WO | WO2011140444 A1 | 11/2011 |

OTHER PUBLICATIONS

International Preliminary Report on Patentability from International Appln. No. PCT/IB2011/054102 dated Mar. 19, 2013.

\* cited by examiner

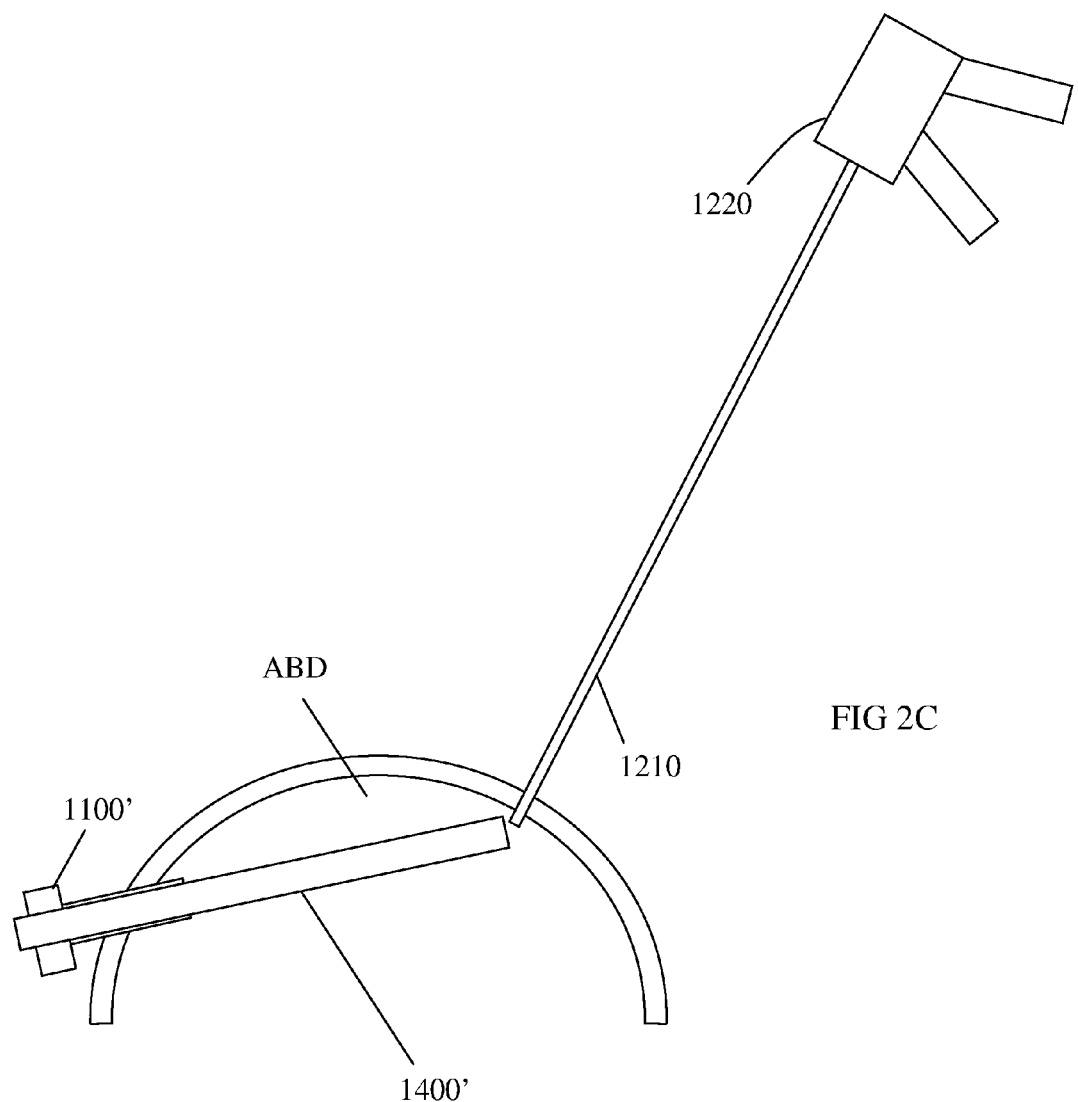
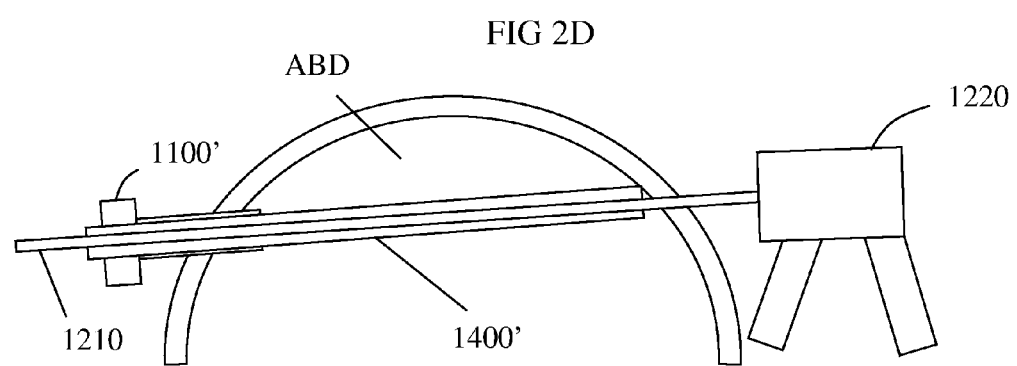

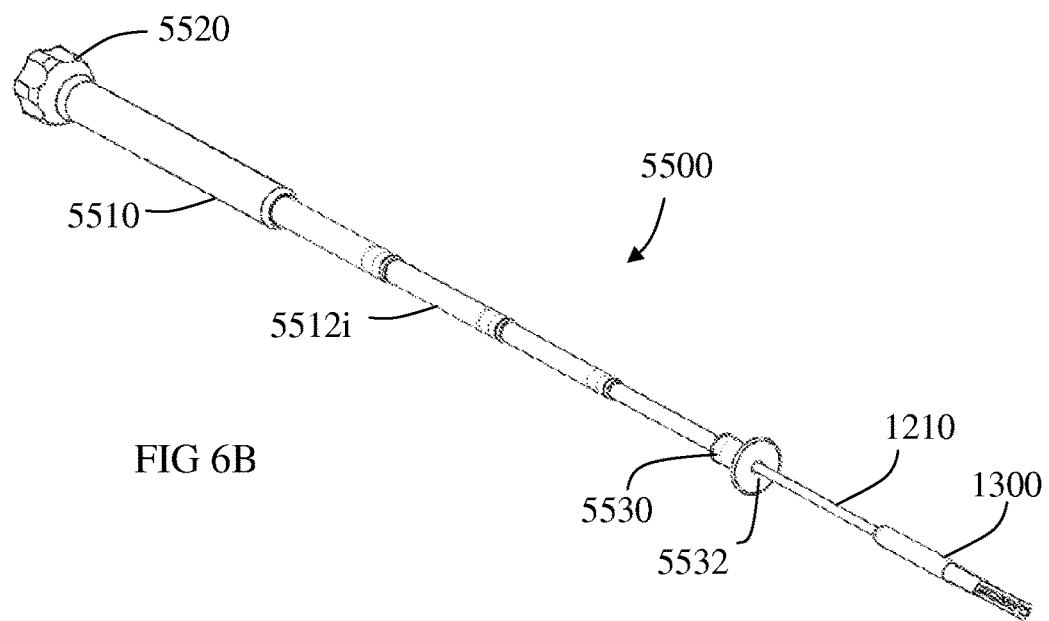
FIG 6B
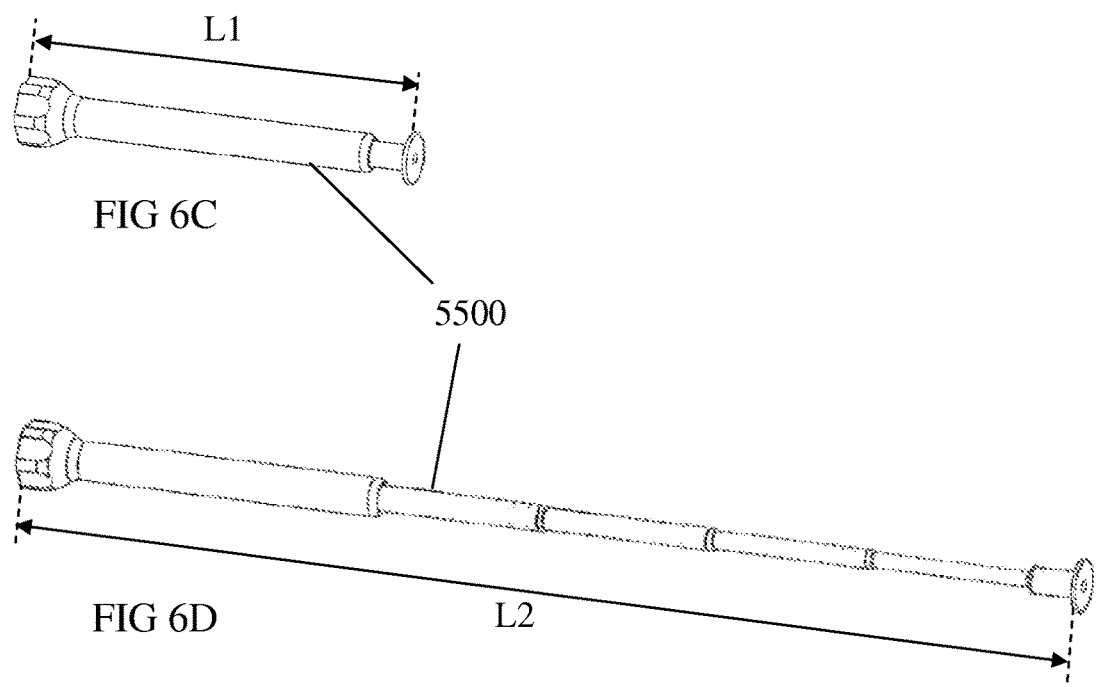
FIG 6C
FIG 6D

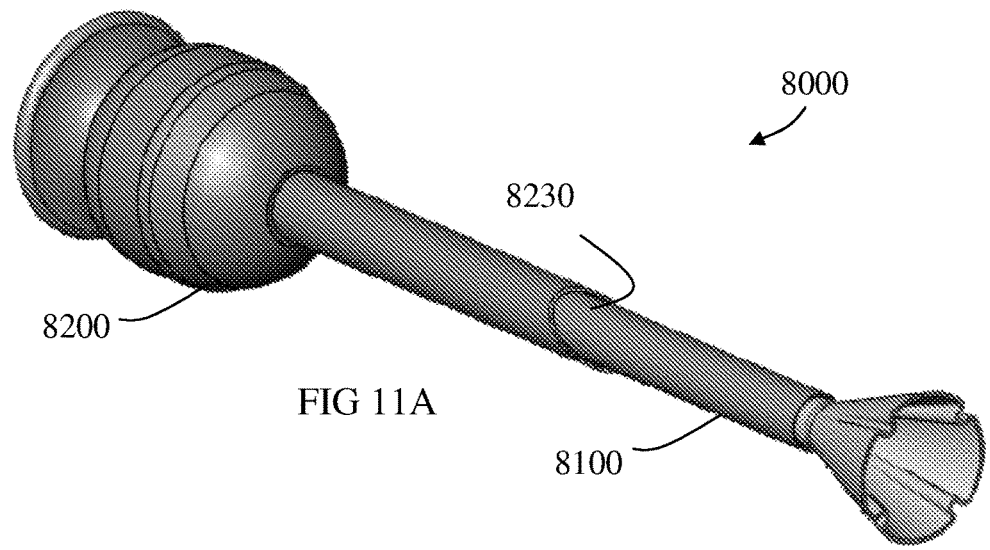
FIG 11A
FIG 11B
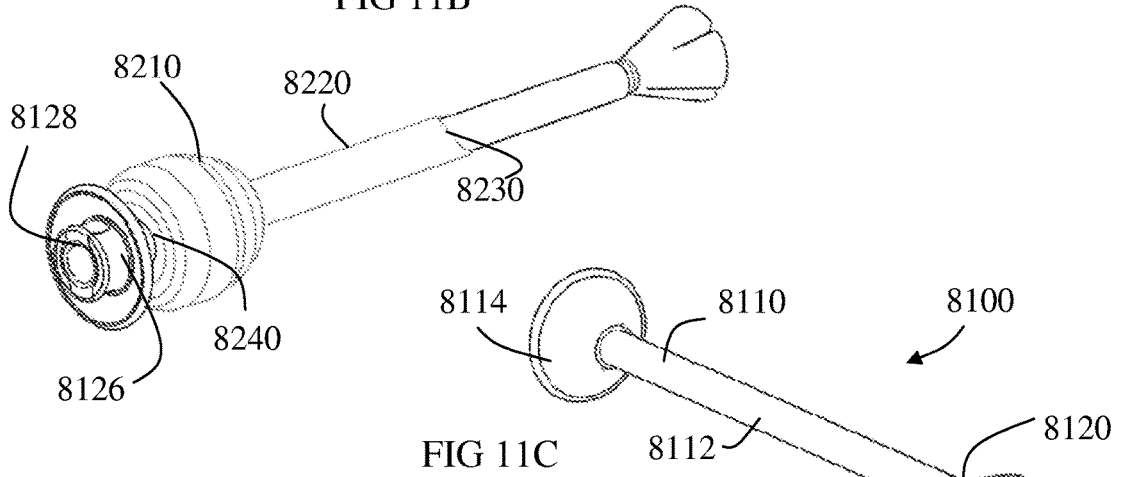
FIG 11C
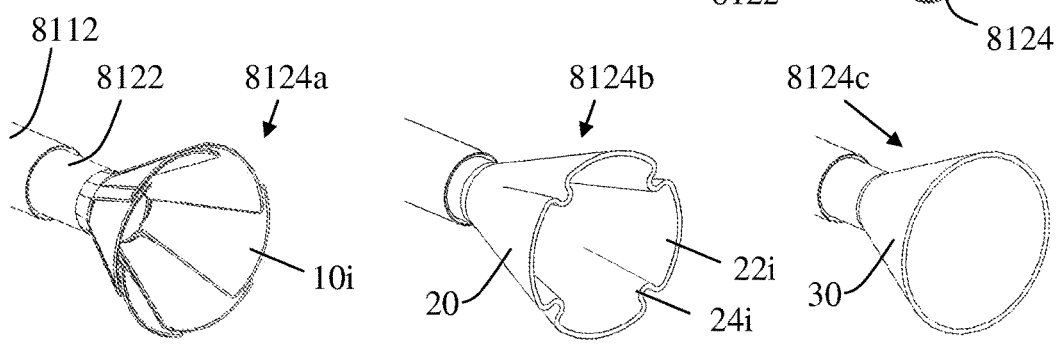
FIG 11D   FIG 11E   FIG 11F

MICRO LAPAROSCOPY DEVICES AND DEPLOYMENTS THEREOF

RELATED APPLICATIONS

This application is a national phase filing under 35 U.S.C. 371 of International Application No. PCT/IB2011/054102, filed on Sep. 19, 2011, which claims the benefit of priority under 35 USC 119(e) of a U.S. provisional application Ser. No. 61/384,288, filed Sep. 19, 2010 and of a U.S. provisional application Ser. No. 61/493,423, filed Jun. 4, 2011, both having the title "MICRO LAPAROSCOPY SYSTEM AND METHOD", the entirety of these applications is hereby incorporated herein by reference for the teachings therein.

The contents of the above documents are incorporated by reference as if fully set forth herein.

FIELD OF THE INVENTION

The present invention generally relates to systems and methods for performing surgeries, and more specifically to methods and devices for laparoscopic surgeries.

BACKGROUND OF THE INVENTION

Laparoscopic or minimally invasive surgery includes the use of several relatively small ports into the abdomen by which different types of instrumentation and accessories are introduced and used for different surgical interventions (usually performed under endoscopic vision). Although usually considered superior in several aspects to open surgery, the use of a plurality of 5 to 15 mm ports still leads to local pain, scars, and possibly port related complications such as hernia in scars and the need for one or two assistants in addition to the surgeon.

In past years, new versions of laparoscopic systems and approaches were introduced to overcome several of the "classic" laparoscopy disadvantages, mainly the Single-Port Access (SPA) and the Needlescopy approaches. In SPA the surgeon operates almost exclusively through a single entry point, typically through the patient's navel, using access ports and hand instrument. Highly experienced and skilled physicians may still use standard laparoscopic hand instruments, although the use of a single port access decreases its triangulation and complicates maneuverability. The use of special-purpose articulating instrumentation was introduced to overcome this difficulty, although it is considered very expensive, necessitates special training and still involves complex surgical maneuverability.

"Minilaparoscopy" (also known as "needelscopic laparoscopy") is intended to overcome the problems encountered in single port access surgery. While the advantages of SPA include improved cosmetic, less abdominal wall pain and less incision related complications, this surgical approach has disadvantages. The vision is partially obscured by the paralleled inserted instruments; there is minimal triangulation and limited maneuverability of the surgical instruments. Minilaparoscopy maintains the same mode of surgery as standard laparoscopy however there is only one sheath and all the rest of the instruments are connected to needle-like shafts which are inserted with no trocar and therefore provide comparable cosmetic and painless results as SPA.

In needlescopy, the laparoscopic ports are replaced with small incisions, usually between 2 to 3 mm in diameter. The surgery is performed by inserting narrow guide tubes into the small incisions and then passing tiny instruments through the tubes, while using a small camera for guidance. The small instruments have very slender tips which make dissection and tissue maneuvering very difficult. Furthermore the instrument tips may have a greater tendency to break and their removal may be cumbersome and difficult.

In order to avoid such difficulties while maintaining small incision porting, it has been advised to combine the single-port and the needlescopic approaches. This is achieved by first inserting regular-sized interchangeable end-effectors through a regular size single port access and then detachably attaching them to corresponding distal portions of needle-sized manipulators. The manipulators are protruding into abdomen cavity via miniature needlescopic type incisions. Locating and engaging between a needle manipulator and an end-effector inside the abdominal cavity may be risky and cumbersome, therefore the Inventors suggest that such engagement and connection will take place in a more secured location such as outside the abdominal cavity or even outside patient's body.

SUMMARY OF THE INVENTION

According to a broad aspect of some embodiments there is provided an apparatus for reversely deactivating a port seal in a laparoscopic port and providing a continuous passage between the laparoscopic port and a remote location in a body cavity. In some embodiments, the laparoscopic port is adapted for deployment over an abdominal cavity.

In an aspect of some embodiments there is provided a laparoscopy system applicable for deploying a detachable end-effector to a distal end of a needle portion of a needle unit. In some embodiments, the system includes a laparoscopic port and at least one of: (1) a reversed port seal, (2) a guiding cannula, (3) a needle portion unit having a needle portion, optionally a proximal needle portion, (4) a needle fortifier apparatus adapted for fortifying the needle portion and (5) a laparoscopic organ retractor. In some embodiments, the guiding cannula is adapted to capture a distal end of the needle portion, whereby the distal end is pulled through the guiding cannula to an outside environment, thereby allow deployment of an end-effector to the distal end of the needle portion. In some embodiments, a camera head is detachably connected to a distal portion of a second needle unit.

In an aspect of some embodiments, there is provided a guiding cannula that includes an elongated tubular member having an outer diameter which is adapted to fit in a lumen of the laparoscopic port having a port seal, the elongated tubular member is introducible through the laparoscopic port while reversely deactivating the port seal. In some embodiments, the elongated tubular member encloses at least one lumen axially extending from a distal opening to a proximal opening. In some embodiments, at least one of the lumens is adapted to receive a laparoscopic device from the distal opening and/or the proximal opening. A laparoscopic device may include at least one of a capturing member, a visual system, a suction tube and a needle portion, optionally a distal needle portion. The at least one lumen may include a minimal diameter equal or higher than 2 mm, optionally equal or higher than 5 mm. In some embodiments, the elongated tubular member is telescopically extendible to any position of a distal end of a needle portion, whereby a passage is obtainable between the distal end of the needle portion and the laparoscopic port.

In some embodiments, the elongated tubular body is provided with means for selectively fixating it in a chosen tridimensional degree in the body cavity.

In an aspect of some embodiments there is provided a sealing member deployable in the laparoscopic port, the guiding cannula, the elongated tubular member, and/or any of its lumens. In some embodiments, the sealing member is a reversed port seal configured to be deployed in the laparoscopic port and arranged for sealing in a direction from a distal opening to a proximal opening in the laparoscopic port; whereby a sealed passage is provided between the body cavity and the outer body environment.

The sealing member may be positionable in the lumen and may include a plug, a covering, a slidable fitting in the at least one lumen while covering at least partially its cross section thereof. In some embodiments, the sealing member is arranged for sealing in a direction from the distal opening to the proximal opening. Optionally, the sealing member includes at least one enclosing member (e.g., a fin-like member hingedly supported in the lumen) adapted to collapse and/or be otherwise reversely deactivated at a travel therethrough from a distal to proximal direction or at both directions.

In some embodiments, the sealing member includes a plug adapted to snugly fit in a proximal entry of the lumen. The plug may be either sealed or may include a minute opening sized for snugly fitting a laparoscopic device, for example a slender endoscope and/or a surgical instrument, to thereby minimize or completely avoid gas migration through the laparoscopic port and/or the guiding cannula, or any of its lumens. The guiding cannula may be provided in a kit includes a plurality of plugs differentiated by passive sealing properties and/or opening sizes thereof.

In some embodiments, the elongated tubular member includes at least two lumens adapted to accommodate at least two laparoscopic devices in parallel. In some embodiments, a first lumen includes a first proximal opening concentric to a first distal opening thereof and a second lumen includes a second proximal opening angled to a second opening thereof. The guiding cannula may be provided in a kit which includes a rigid endoscope fitting in the first lumen and a pliable tube fitting in the second lumen optionally connectable to a fluid suction and/or pressurizing means.

In some embodiments, the elongated tubular member having a maximum protrusion length to reach the needle portion at its entry point. Accordingly, the elongated tubular member is telescopically extendible to a farthest point on an opposite wall portion in a body cavity. The elongated tubular member of the present invention may be substantially straight and/or bendable to a chosen shape between the laparoscopic port and a chosen point adjacent or on a wall portion of a body cavity.

Means positioned at a distal portion of the elongated tubular member or otherwise provided therethrough may be used to facilitate, ease and/or control the capturing and the optional pulling therein of the needle portion. In an aspect of some embodiments, there is provided in a laparoscopic system, a selectively operable capturing means adapted to capture an end portion of a needle projecting from an entry point to a body cavity distant to a deploying position of the laparoscopic port in the body cavity. In some embodiments, the capturing means includes an elongated member having an expandable and/or contractible end portion.

In some embodiments, a laparoscopic device of the present invention is introducible an elongated tubular member lumen. In some embodiments, the laparoscopic device is provided at a remote location in the body cavity and is insertable to a distal opening of the lumen. Such a distally insertable laparoscopic device may include a maximal diameter equal or smaller than 3 mm. Alternatively, the laparoscopic device is provided at the laparoscopic port and includes a maximal diameter of 10 mm or less, optionally 5 mm or less.

In some embodiments, the laparoscopic device comprises an elongated slender body and a collapsible member (e.g., a loop, a snare, a grasper or a magnet) and optionally the collapsible member of the laparoscopic device is adapted to at least one of project through the distal opening, capture a distal end of a needle portion, collapse and guide the needle portion into the elongated tubular member and out through the proximal opening.

In some embodiments, the distal end of the elongated tubular member includes a portion having a selectively extendable and/or contractible edge for guiding the needle portion into the elongated tubular member and out through the sealing member. In some embodiments, the extendable and/or contractible edge is at least partly funnel shaped when extended and/or may be selectively altered using actuating means. In some embodiments, the extendable and/or contractible edge includes a non-expandable proximal end and an expandable distal edge. In some embodiments, the extendable and/or contractible edge includes a distal expandable portion that is expandable to at least double the diameter of the non-expandable proximal end and/or to a maximal diameter equal or larger than 20 mm.

In some embodiments, actuating means for the selectively extendable and/or contractible edge may comprise an outer tubular portion slidable over a snugly fitted inner tubular portion and wherein the outer tubular portion is adapted to selectively cover or uncover a portion of the extendable and/or contractible edge. Optionally, the extendable and/or contractible edge is self-expandable to an expanded shape and/or contractible, optionally to a cylindrical shape. In some embodiments, the extendable and/or contractible edge comprises an iris diaphragm includes a plurality of overlapping petal like members. Optionally, additionally or alternatively, the extendable and/or contractible edge comprises a plurality of crimps allowing symmetrical collapsing from a funnel shape to a cylindrical shape. Additionally or alternatively, the extendable and/or contractible edge includes a smooth surface which thereby facilitates unhindered sliding motion of the needle portion into the elongated tubular member while aligning the needle portion with a longitudinal axis thereof. Optionally, the smooth surface is adapted to withstand cleaving by a sharp needle tip.

In some embodiments, at least one lumen has arranged therein a visual system, such as an endoscope. Alternatively or additionally, other visualizing means may be introduced into the body cavity such as a camera (e.g., a detachably attached camera head positioned on a distal end of a second needle), which may be used to monitor deployment process and/or any steps thereof, including locating the needle portion and/or its entry point to the body cavity, engaging the needle portion, entrapping it and pulling/pushing it through the guiding cannula.

In an aspect of some embodiments, there is provided a laparoscopy system for deploying a detachable laparoscopic end-effector to a distal end of a slender shaft manipulator. In some embodiments, the system includes a cannula adapted to provide a sealable passage between a body cavity and an outer body environment. In some embodiments, the laparoscopy system includes capturing means provided through the cannula and adapted to travel in and out the cannula, capture the distal end and pull thereof outside the body cavity to the outer body environment through the cannula, whereby a detachable laparoscopic end-effector may be deployed to the distal end under direct vision. In some embodiments, the capturing means includes at least one loop, optionally two loops. In some embodiments, at least one loop is provided with bonding or clinging means.

In some embodiments, a detachable camera head is provided attachable to an elongated manipulator and maneuverable in the body cavity to a direct visualization angle to the distal end capturing and/or pulling.

In an aspect of some embodiments, there is provided a needle fortifier apparatus includes a plurality of telescopically connected tubular members, wherein the plurality of telescopically connected tubular members are axially slidable arranged, and the plurality of telescopically connected tubular members is enclosing a lumen adapted to at least partly accommodate a needle portion of a needle unit. In some embodiments, the needle fortifier apparatus comprises a proximal connector adapted to connect to an actuator portion of the needle unit. Optionally, additionally or alternatively, the needle fortifier apparatus includes a distal end having a brim-like surface adapted to abut to a skin surface. In some embodiments, the brim-like surface is adapted to continuously abut and/or engage the skin surface during use. The brim-like surface may include a bonding element to the skin surface. In some embodiments, the plurality of telescopically connected tubular members is self-extendable to a maximal extended form. Optionally, alternatively or additionally, the plurality of telescopically connected tubular members is fixedly extendable or contractible to a chosen length and in some embodiments, may be provided as a laparoscopic organ retractor which further comprises a grasper adapted for grasping body tissue and/or organ connectable or readily connected to a needle unit.

In an aspect of some embodiments, there is provided a method for deploying a detachable end-effector to a distal end of a needle portion of a needle unit, the method includes at least one of the following steps: providing a laparoscopic port having a port sealing element; filling a body cavity with gas; introducing a guiding cannula being an elongated tubular member through the laparoscopic port while reversible deactivating the port sealing element; adjusting the guiding cannula telescopically for approaching the distal end of the needle portion; creating a passage between a position of the needle portion and the laparoscopic port; passing the distal end to an outer body environment through the guiding cannula by passing a second sealing element arranged in a lumen of the guiding cannula; and deploying the end-effector to the distal end of the needle portion.

The method may include a step of capturing the distal end of the needle portion and pulling it into the guiding cannula. The capturing is performed using a capturing member includes an expandable and/or contractible edge, whereas a capturing member includes at least one of a loop, a snare, a grasper and a magnet.

The method may include a step of withdrawing the distal end having the end-effector back into the body cavity.

The method may include a step of removing the guiding cannula before deploying the end-effector, whereby the needle portion is accommodated in the laparoscopic port being sealed by the port sealing element.

In an aspect of some embodiments, there is provided a method for deploying a laparoscopy system in a body cavity, the laparoscopy system includes a slender shaft manipulator having a distal end and a detachable laparoscopic end-effector connectable with the distal end, the method includes at least one of the following steps: providing a laparoscopic port; filling the body cavity with gas to meet a chosen inflation volume; providing reversed sealing means in the laparoscopic port thereby allowing sealed passage therethrough from within the body cavity to an outer body environment; passing the distal end from the body cavity through the laparoscopic port to the outer body environment; and attaching the detachable laparoscopic end-effector to the distal end.

In some embodiments, the reversed sealing means prevents excessive migration of gas from the body cavity via the laparoscopic port thereby maintaining the chosen inflation volume throughout the deploying.

The method may include at least of providing a channel between the laparoscopic port and the distal end, the channel having a length allowing extending over to the distal end, and a lumen extended across the length sized to accommodate a travel of the distal end therethrough; and engaging the channel with the distal end thereby providing a closed passage thereto through the laparoscopic port.

In an aspect of some embodiments, there is provided a method for connecting a detachable end-effector to a distal end of a slender shaft manipulator, includes at least one of the following steps: inserting the distal end into a body cavity through a first opening; inserting a guide into the body cavity through a sealed sheath deployed at a second opening and extending the guide to engage with the distal end; passing the distal end through the sheath to an outer body environment; and connecting the detachable end-effector to the distal end. In some embodiments, the guide includes an expandable distal edge and the method includes the step of expanding the guide edge.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 2C-D illustrate different deployment stages of a third schematically illustrated exemplary micro-laparoscopic system, in accordance with an exemplary embodiment of the invention;

FIGS. 6B-D, illustrate isometric views of an exemplary external telescopic needle fortifier unit 5500, in accordance with an exemplary embodiments of the present invention;

FIGS. 11A-F illustrate different views of an exemplary laparoscopic system and members thereof, in accordance with exemplary embodiments of the present invention;

DETAILED DESCRIPTIONS OF EXEMPLARY EMBODIMENTS

Figure 1A:
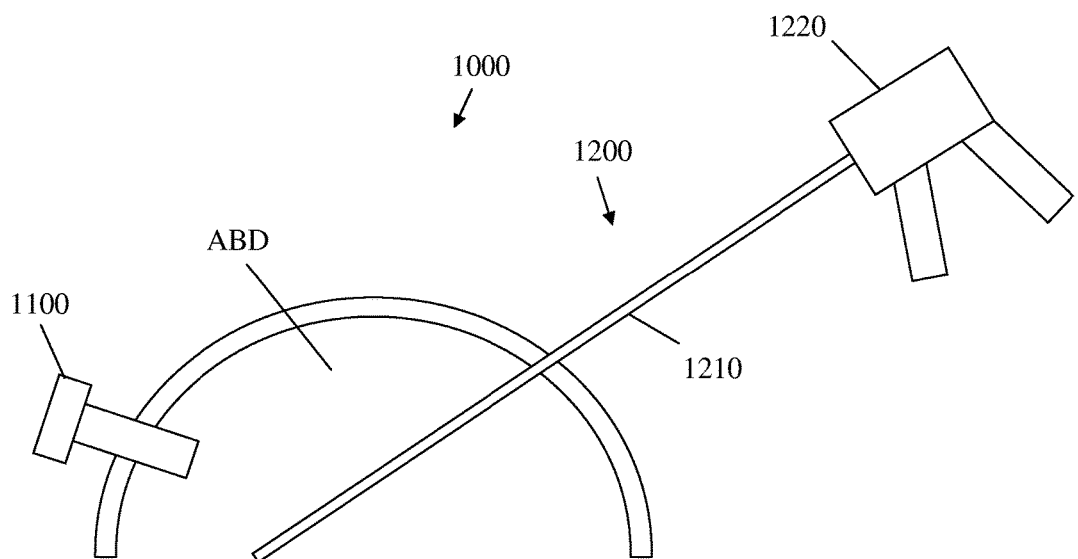
FIGS. 1A-D illustrate different deployment stages of a first schematically illustrated exemplary micro-laparoscopic system, in accordance with an exemplary embodiment of the invention.

It is understood that the invention is not limited to the particular methodology, protocols, and reagents, etc., described herein, as these may vary as the skilled artisan will recognize. It is also to be understood that the terminology used herein is used for the purpose of describing particular embodiments only, and is not intended to limit the scope of the invention. It also is to be noted that as used herein and in the appended claims, the singular forms "a," "an," and "the" include the plural reference unless the context clearly dictates otherwise. The embodiments of the invention and the various features and advantageous details thereof are explained more fully with reference to the non-limiting embodiments and examples that are described and/or illustrated in the accompanying drawings and detailed in the following description. It should be noted that the features illustrated in the drawings are not necessarily drawn to scale, and features of one embodiment may be employed with other embodiments as the skilled artisan would recognize, even if not explicitly stated herein. Descriptions of well-known components and processing techniques may be omitted so as to not unnecessarily obscure the embodiments of the invention. The examples used herein are intended merely to facilitate an understanding of ways in which the invention may be practiced and to further enable those of skill in the art to practice the embodiments of the invention. Accordingly, the examples and embodiments herein should not be construed as limiting the scope of the invention, which is defined solely by the appended claims and applicable law. Moreover, it is noted that like reference numerals reference similar parts throughout the several views of the drawings.

The following preferred embodiments may be described in the context of exemplary laparoscopic surgical procedures for ease of description and understanding. However, the invention is not limited to the specifically described devices and methods, and may be adapted to various clinical applications without departing from the overall scope of the invention. For example, devices and related methods including concepts described herein may be used for deployment and/or activation of systems and/or devices for surgical procedures such as but not limited to: gynecology surgery, thoracic surgery, abdominal surgery, orthopaedic surgery, general minimally invasive intrusive procedures and others.

The present invention generally relates to systems and methods for performing surgeries, and more specifically to methods and devices for laparoscopic surgeries. According to a broad aspect of some embodiments there is provided an apparatus for reversely deactivating a port seal in a laparoscopic port and providing a continuous passage between the laparoscopic port and a remote location in a body cavity. In some embodiments, the laparoscopic port is adapted for deployment over an abdominal cavity.

An aspect of some embodiments of the present invention relates to means and surgical techniques for providing an encased passage for easily and safely traveling a tissue-affecting device from within a bodily chamber to an outside body environment. An encased passage may be any guiding and/or channeling apparatus (e.g., a guiding cannula) having constant or variable cross section and/or shape, and/or which may at least along part of its length fit in a normally sealed port, such as a laparoscopic port, connecting between the body chamber and the outside environment.

A tissue affecting device may be any surgical instrument or other device which may actively or passively harm, modify or otherwise affect a live tissue in direct contact and/or when operated, for example, a surgical needle or other slender instrumentation which may include a sharp or blunt distal tip. A tissue affecting device may otherwise be provided as an end-effector device which may be detachably connectable to a distal end of a tool manipulator, such as a needle portion of a needle unit.

In the present invention, "distal" shall mean away from an operator hand and towards or inward the patient's body, whereas "proximal" shall refer to a proximity to operator and away from within the body. The distal portion, end or tip of a needle, as in the present invention, include a manually or robotically operable manipulator which comprises a slender rod- or tube-like shaft that is connected or detachably connectable to a surgical tool (e.g., an interchangeable surgical head). An encased passage according to the present invention shall facilitate travel of a bare manipulator slender shaft entering a body chamber or cavity from a first entry-point or port, and through a second remote port, to an outer body environment, while diminishing or completely avoiding affecting any tissue or internal organ. When a distal end of the manipulator shaft projects outside the body it may then be deployed, functionalize or otherwise be attached with a surgical head, and then pulled back into the body chamber.

Beside the safety consideration, the encased passage may alternatively or additionally facilitate a chosen track or course for the tissue affecting device to follow, thereby easing and controlling its travel from within the body to the outside environment.

Optionally, alternatively or additionally, the encased passage may be provided sealed and/or be selectively sealable at least during part the tissue affecting travel therethrough. A common practice in abdominal related surgeries (such as in laparoscopic surgeries) is to inflate the abdominal cavity with inert gas and to maintain it in sufficient inflation throughout the procedure in order to allow more space for the operation and tool maneuvering and to move internal organs or other tissues away from each other. In laparoscopy, the cannulae or ports are then provided with sealing means which allow insertion and travel therethrough of endoscope, surgical instruments, suction and other devices from the outside-in with minimal to none gas escape. Nevertheless, in embodiments of the present invention, a reversed travel of a device from the inside-out through a known, common or commercially available laparoscopic port may harm or dysfunction the port sealing means and may even stuck within. Therefore, an encased passage of the present invention may be used to pass through, bypass and/or deactivate or alter a laparoscopic port sealing means to a low a reversed passage, and/or to facilitate a selective and/or continuously sealed environment to a device travel from inside the body and out.

In some embodiments, the encased passage of the present invention can be facilitated from and in between a port (e.g., a laparoscopic port) and any chosen location in a body chamber communicating with the port. In some embodiments, the encased passage is extendable or otherwise creatable between at least two distant ports, incisions or any other entry regions in a single body chamber, such as the abdominal cavity. Accordingly, it may be advantageous to only minutely protrude the body chamber with the tissue affecting device and engage and/or entrap it with and/or in the encased passage thereby avoiding even the smallest less/un-safe and/or less/un-controlled travel in the body chamber. In some embodiments, added capturing or trapping means may be used to ease, improve and/or control engagement, connecting, conveying and/or aligning the tissue affecting device with respect and into an encased passage entry. Such capturing means may be connected to or part of a distal portion of the encased passage, and may be for example an expandable portion which may or may not be shaped to a form (e.g., a funnel shape) which improve inward channeling of the captured device. Additionally or alternatively, capturing means may be introduced apart, alongside or through the encased passage for the capturing. Capturing may be passive (such as in the case of expanding a distal portion to a funnel shape) or active (such as by providing selectively constricting, grasping or looping means (e.g. a snare) to actively connect to and trap the target device in the body chamber).

Other means are also described which may be used to assist in deployment, delivery, control and surveillance, and/or used for the surgical intervention.

Referring now to the drawings, FIGS. 1A-D illustrate different deployment stages of a first schematically illustrated exemplary micro-laparoscopic system 1000, in accordance with an exemplary embodiment of the invention. System 1000 is deployed prior to utilization in a body cavity, optionally abdominal cavity ABD. System 1000 includes a laparoscopic working channel, trocar or port, referred to as sheath 1100, and at least one handheld micro-laparoscopic manipulator referred to as needle unit 1200. Needle unit 1200 includes a needle portion 1210 and an operation handle 1220. Needle portion 1210 is configured to be attached at its distal end to a detachable and/or an interchangeable surgical end-effector or tool 1300 (shown in FIG. 1C).

Figure 1B:
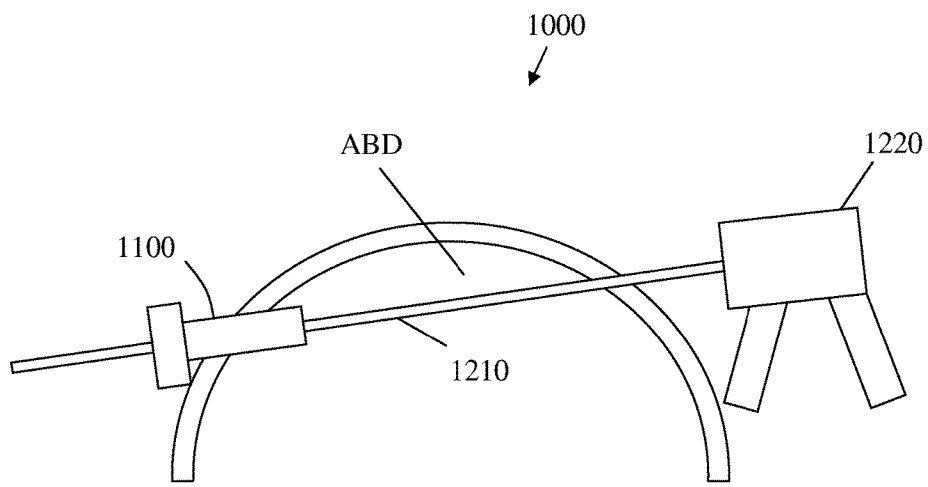
Figure 1C:
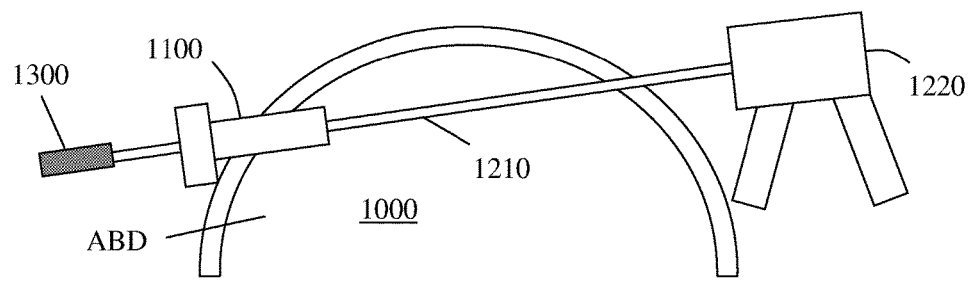
Figure 1D:
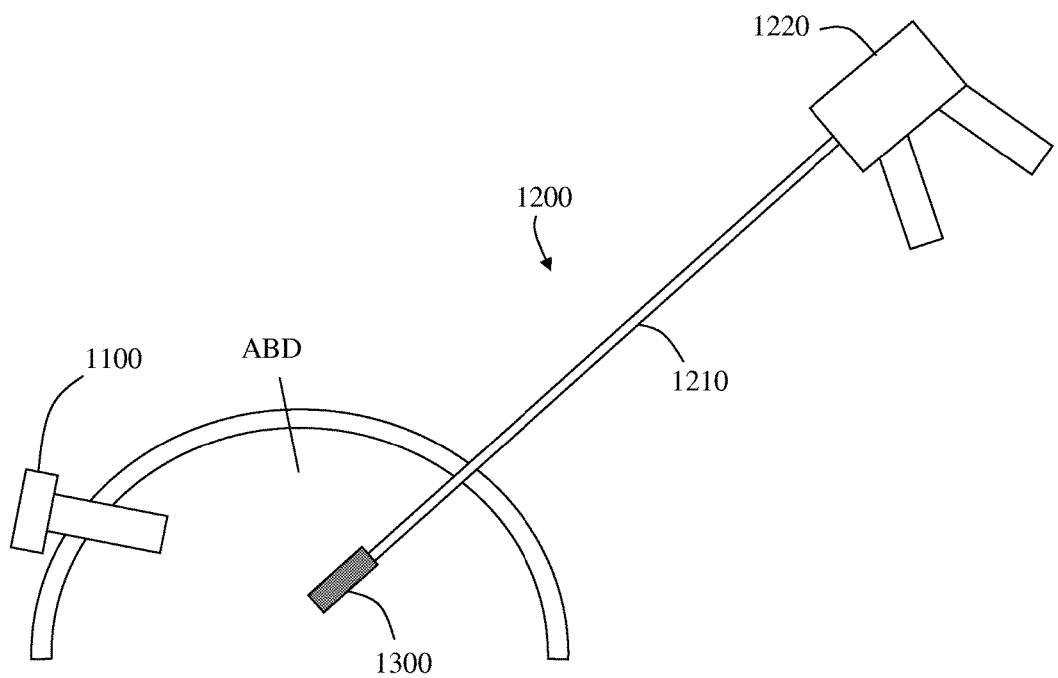

In FIG. 1A, sheath 1100 and needle unit 1200 are positioned after insertion into abdominal cavity ABD and prior to attaching tool 1300. Optionally, sheath 1100 houses an endoscope (not shown) for visualization and optionally is connected with a trocar and/or other sharp means provided for establishing penetration. In order to attach tool 1300 to distal end of needle portion 1210, the surgeon may pass it through the lumen of sheath 1100 to an outer body environment (as shown in FIG. 1B) by aiming towards the endoscope lens (or "towards his eye" as seen in the monitor). Before or during needle portion 1210 travel through sheath 1100 lumen, the endoscope is withdrawn. Next, as shown in FIG. 1C, tool 1300 is connected, optionally manually, to needle portion 1210. Then, needle unit 1200 together with tool 1300 is pulled back into abdominal cavity ABD and the surgical intervention or step may begin. Alternatively or additionally, sheath 1100 may be applied to deliver resected body tissues therethrough using needle portion 1210 with tool 1300.

Tool 1300 may be any operational element (e.g., a probe or an instrument) deployable within a body, including but not limited to: surgical tools, grasping elements, dissectors, needle holders, clippers, scissors, connecting (e.g., stapling) elements, biopsy related instruments, sensor elements, imaging elements, clamping, clipping elements or grasping devices, heat generating probes (including RF, laser, IR, light, etc.), cryogenic probes, illuminating elements cutting and dissecting devices or energy sources, ultrasound probes, camera or other imaging probes, lenses, lenses tubes, or any other optical instruments, etc.

In some embodiments, sheath 1100 includes an air-tight two-way valve or other sealing mechanism (not shown) that can allow traveling of instrumentation therethrough in both directions totally or significantly without derived loss of air/gas (usually but not necessarily—$CO_2$) previously and/or continuously introduced to abdominal cavity ABD. Such a sealing mechanism should collapse or withdraw when a needle or other slender shaft component slides either from a proximal side to a distal side or vice versa and engages with it along its travel. The definition of "air-tight" or "sealed" with respect to a port, a lumen, a passage, a valve or to any other opening or device containing an opening, which allows direct communication between a body chamber (e.g., abdominal cavity, stomach or others) and an outer environment (e.g., outside patient's body), refers in this invention either to a substantially sealed passage to gas travel therethrough from the body chamber to the outer environment, or to a decrease in its flow rate to be substantially equal to a gas inflation rate continuously or sequentially supplied to the body chamber by auxiliary means.

Sheath 1100 may be of any preferred size, and usually between 3 to 20 mm in diameter, optionally about 10 mm or 12 mm (e.g., similar in size to regular laparoscopic port). Sheath 1100 may be sized (e.g., smallest cross section) to accommodate a largest of a surgical tool in a specific tool kit. In some embodiments, system 1000 includes a single regular-sized laparoscopic port that may be utilized for tool(s) 1300 insertion into body and/or connection to needle unit 1200.

In some embodiments, needle portion 1210 includes a distal tip. Needle portion and tip largest cross section may be 0.5 to 5 mm in diameter, optionally 1 to 2.5 mm, optionally about 1 mm, about 1.5 mm or about 2 mm or higher or lower or intermediate. Needle tip is optionally sharp and/or pointed in order to allow at least one of tissue penetration and easier engagement with tool 1300. Optionally, needle tip is a Veres needle which optionally permits penetration through skin and abdominal wall tissue while preventing injury of internal organs (e.g., bowels) when not "armed". Alternatively, needle tip is substantially blunt. Optionally, needle portion 1210 includes interlocking means, e.g., threading or a groove for snap-locking (not shown), for firmly connecting with tool 1300, or alternatively by any means of friction, pressure or other means known to art. Handle 1220 may be any manually operated type laparoscopic instrumentation handle or may be replaced with any robotic or other non-manually operated arm. In some embodiments, handle 1220 includes mechanisms which operates tool 1300 and/or their association (e.g., locking or releasing modes or operations).

At least part of the instruments are made from rigid biocompatible materials as known to a person skilled in the art, and may include stainless steel, optionally hardened or reinforced by carbon coating or fibers, ceramic materials, plastic/polymeric materials (e.g., PEEK), composite materials (e.g., carbon-epoxy), or any combination thereof.

In some embodiments, system 1000 further includes at least one, and optionally at least two, intraoperative imaging devices (e.g., microcameras and/or endoscopes). Optionally, a grasped microcamera is transferred into body via sheath 1100 and attached to one of needle units 1200 which locates it in a preferred position to monitor the surgical operation and/or system deployment. Other microcameras and/or endoscopes may be deployed in other locations using different manipulators.

Figure 2A:
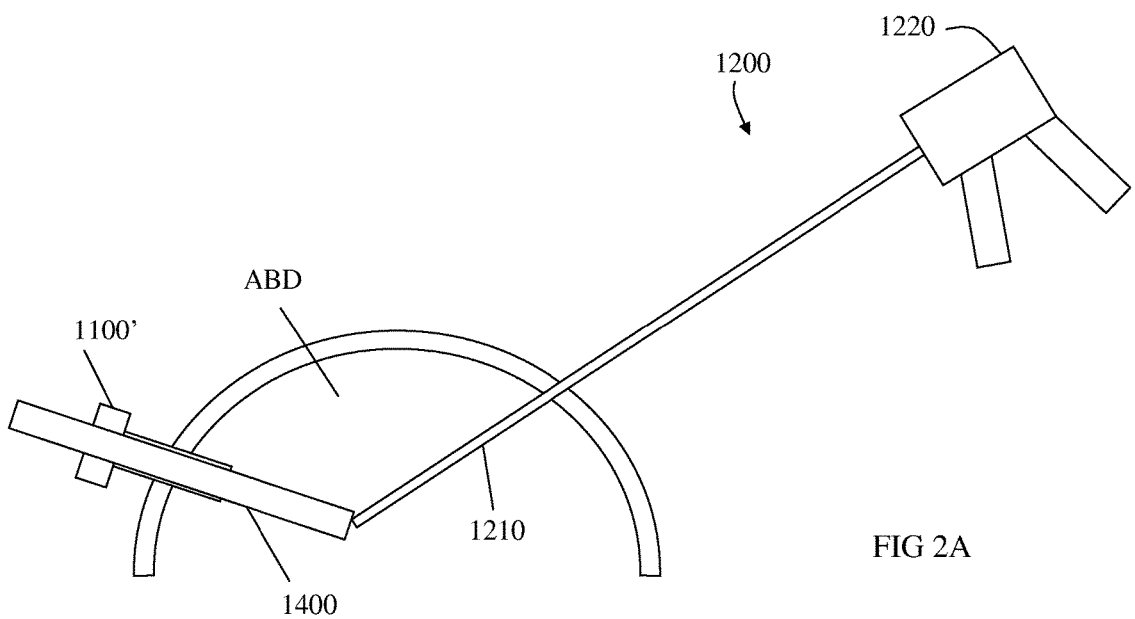
FIGS. 2A-B illustrate different deployment stages of a second schematically illustrated exemplary micro-laparoscopic system, in accordance with an exemplary embodiment of the invention.
Figure 2B:
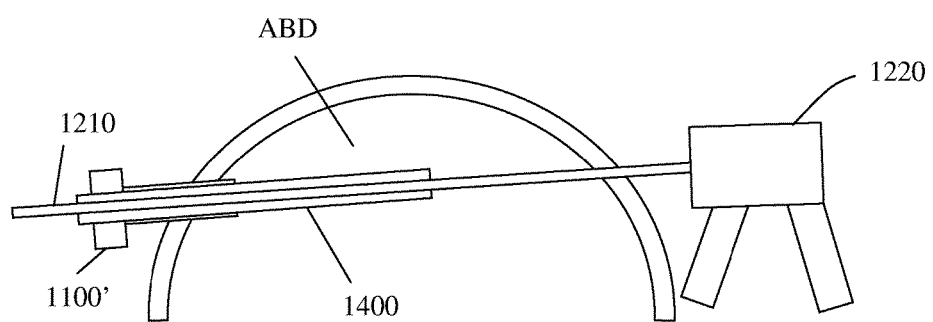

In some situations, the process of maneuvering needle unit 1200 until locating and traveling through sheath 1100 may be difficult, time consuming and/or unsafe, due to the possibility that the needle may harm adjacent tissues. Reference is now made to FIGS. 2A-B, illustrating different (partial) deployment stages of a second schematically illustrated exemplary micro-laparoscopic system, in accordance with an exemplary embodiment of the invention. In this embodiment, a new instrumentation is utilized, namely guiding cannula 1400, which assists with locating and guiding distal end of needle portion 1210 therethrough and on to the outer body environment in a safer approach. Guiding cannula 1400 is telescopically introduced via a sheath 1100', and travels into abdominal cavity ABD until it is adjacent the distal end of needle portion 1210 (as shown in FIG. 2A). Needle portion 1210 may then be inserted into a lumen opening (not shown) of guiding cannula 1400 until it is protruding outwardly into the outer body environment (as shown in FIG. 2B) for a safe and easy placement of tool 1300 thereto, as previously described in FIG. 1C. In this embodiment, an endoscope (not shown) may be placed inside guiding cannula 1400 and/or sheath 1100'. Inner diameter (e.g., lumen diameter) of guiding cannula 1400 may be about 3 to 10 mm, or optionally about 8 mm; and its outer diameter may be about 4 to 13 mm. In some embodiments, additionally or alternatively to using guiding cannula 1400, other locating and/or guiding and/or grasping/connecting devices (not shown) may be used to locate and/or guide and/or grasp needle portion 1210 in abdominal cavity ABD and assist or use in transferring it through sheath 1100' to outer body environment.

FIGS. 2C-D suggest a slightly different approach using a substantially longer or more distally advancable guiding cannula 1400', which is sized and/or configured to reach at or adjacent the inlet/incision of needle 1200 through and into abdominal cavity ABD, so the needle tip may be captured at its entry and not more deeply inside abdominal cavity ABD. In some instances it will be preferable to use this approach, as may be important not only to prevent injury to organs but also to prevent working against the direction of viewing which may be considered cumbersome.

Figure 3A:
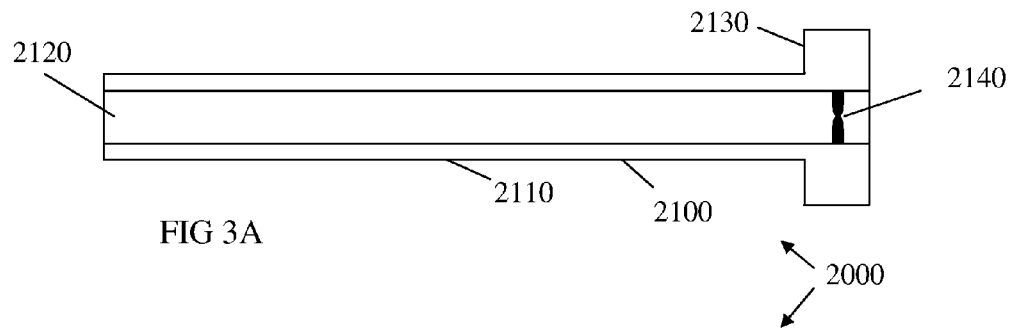
FIGS. 3A-D illustrate different deployment stages of a laparoscopic trocar system, in accordance with an exemplary embodiment of the invention.
Figure 3B:
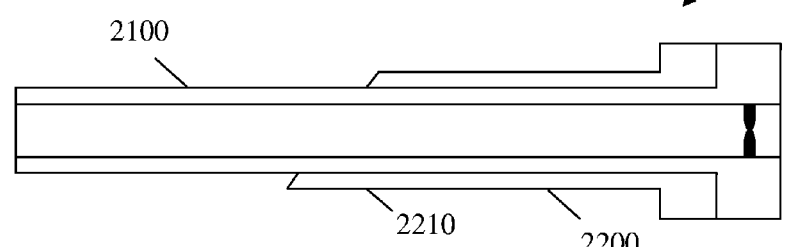

Reference is now made to FIGS. 3A-D illustrating different deployment stages of a laparoscopic trocar system 2000, in accordance with an exemplary embodiment of the invention. As previously described with respect to FIGS. 2A-B and 2C-D, trocar system 2000 includes a sheath 2200 and a mating guiding cannula 2100 sized and configured to travel therethrough. In FIG. 3A, guiding cannula 2100 is shown separately and in FIG. 3B it is shown in a deployment form where it is telescopically mating and/or fastened to sheath 2200. Guiding cannula 2100 includes an elongated body 2110, optionally tubular, with a lumen 2120 passing along its length. At its proximal end there is a lateral extension 2130 which facilitates and improved grasping thereof and/or an inward traveling limiting through sheath 2200. Lumen 2120 also includes an air-tight valve 2140, optionally a two-way valve or a valve which allows only proximal penetration thereto, located along its passage, optionally at its proximal side. Alternatively or additionally to a valve, such as valve 2140, there can be provided a cover (not shown) which will seal or substantially decrease gas travel through lumen 2120, but may be selectively removed and placed according to need.

Figure 3C:
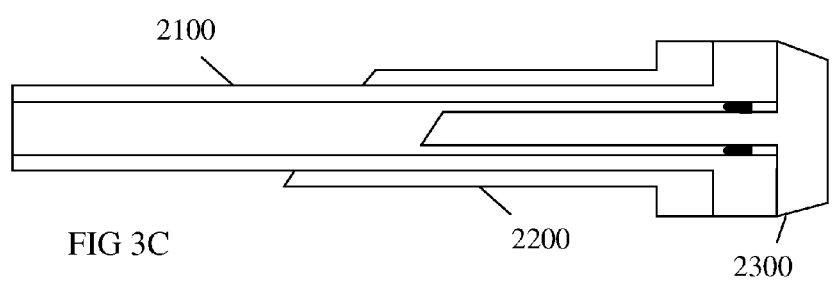
Figure 3D:
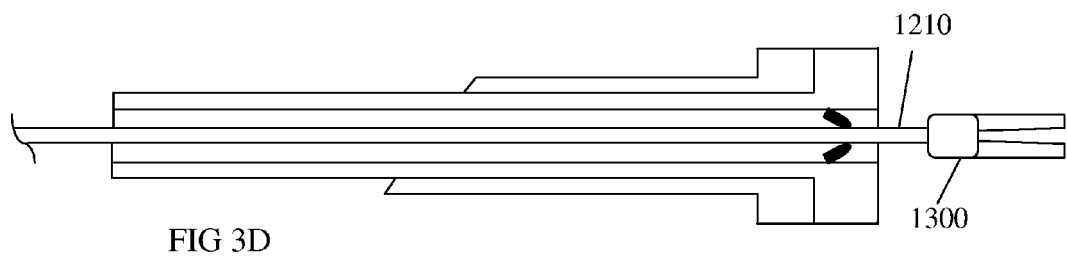

An instrumentation kit (not shown) may include a single guiding cannula or several ones differentiated by lengths, which may vary for example between 4 cm and 50 cm. Guiding cannula 2100 may be substantially rigid or substantially flexible, at least in part. Guiding cannula 2100 may include a widening (not shown) at its distal end for improving accommodation of a needle portion distal end. In some embodiments, guiding cannula 2100 is substantially transparent, at least in part, to allow improved visualization by an endoscope 2300 traveling therethrough (as shown in FIG. 3C), and/or to ascertain by direct vision of the surgeon that the needle tip within the cannula is safely positioned in the sheath and positioned as requested. Endoscope 2300, or any other device delivered distally through lumen 2120, interacts with valve 2140 so that the lumen passage is maintained sealed to outside environment. Endoscope 2300 may be connected and applied during locating and/or guiding phases of needle portion 1210, while before, during or after said location or guiding, endoscope 2300 may be removed to allow a complete travel of needle portion 1210 until sufficiently outwardly projecting onto an outer body environment. In FIG. 3D, needle portion 1210 is shown in such a sufficient projection and already connected with tool 1300 (shown for exemplary purposes only as a grasper). Needle portion 1210, or any other device delivered proximally through lumen 2120, interacts with valve 2140 in such a way the lumen passage is kept sealed to outside environment. Same may apply when needle portion 1210 is pulled back into abdominal cavity ABD with a substantially greater sized tool 1300.

At some instances it may be preferred to seal the cannula around the endoscope. When the tip of the needle is beyond the proximal or exterior end of the sheath, the cannula with the endoscope are removed together and the needle tip is left protruding through the proximal or exterior end of the sheath. Then the effector is connected manually to the tip and pulled back into the abdominal cavity.

Figure 4A:
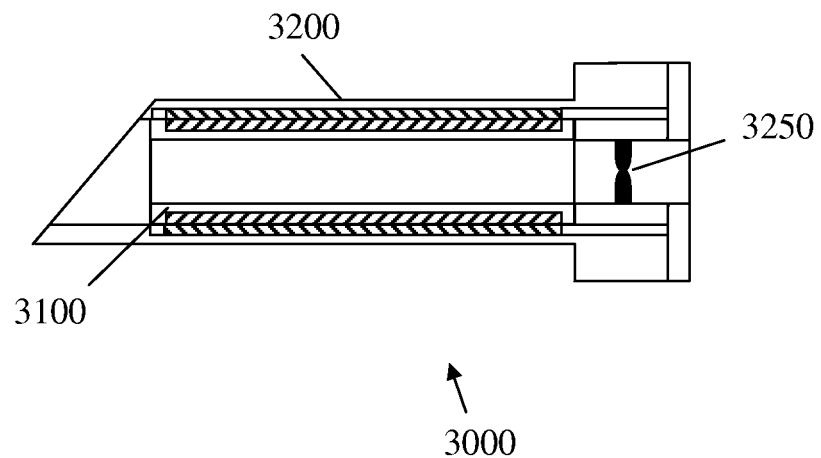
FIGS. 4A-B illustrate different deployment stages of a telescopic laparoscopic trocar unit, in accordance with an exemplary embodiment of the invention.
Figure 4B:
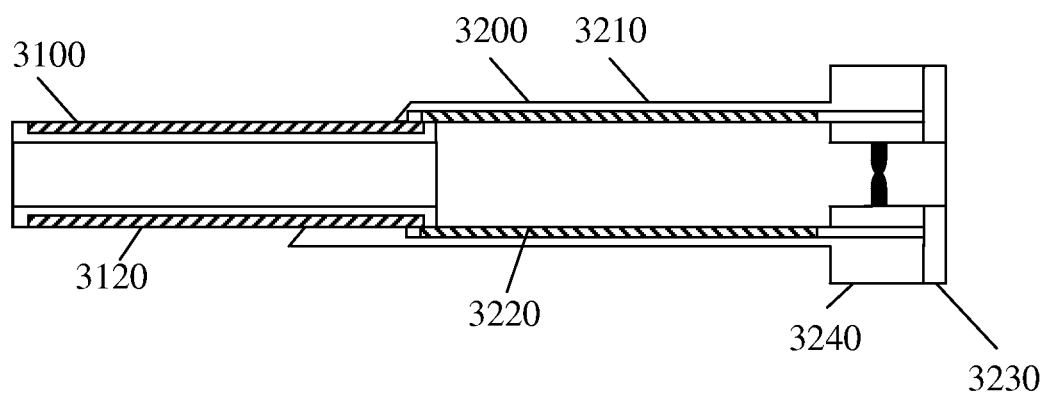

Reference is now made to FIGS. 4A-B illustrating different deployment stages of a telescopic laparoscopic trocar unit 3000, in accordance with an exemplary embodiment of the invention. Trocar unit 3000 includes an inner sleeve 3100 telescopically positionable in an outer sleeve 3200, selectively, from a fully collapsed position (shown in FIG. 4A) to a fully extended position (shown in FIG. 4B) or to any intermediate position therebetween. In some embodiments, relative positioning between inner sleeve 3100 and outer sleeve 3200 is accomplished using a bolt and nut mechanism. In some embodiments, inner sleeve 3100 includes a threaded outer portion 3120 whereas outer sleeve 3200 includes an inner revolving member comprising a threaded portion 3220 and a switch 3230, the inner revolving member is capable only to revolve around its longitudinal axis but incapable of advancing forward or backward along this axis. In such a way, when switch 3230 is revolved clockwise inner sleeve 3100 moves distally and vice versa. Optionally, revolving is done using a motorized mechanism as known in the art. In some embodiments, an air-tight two-way valve 3250, similar or identical to valve 2140, is present, optionally positioned in trocar unit 3000 proximal end 3240, thereby facilitating bidirectional travel of tools, devices (i.e., endoscope) and body tissues therethrough, in such a way the lumen passage is sealed to outside environment and inflation gas filling abdominal cavity ABD may not escape.

Figure 5A:
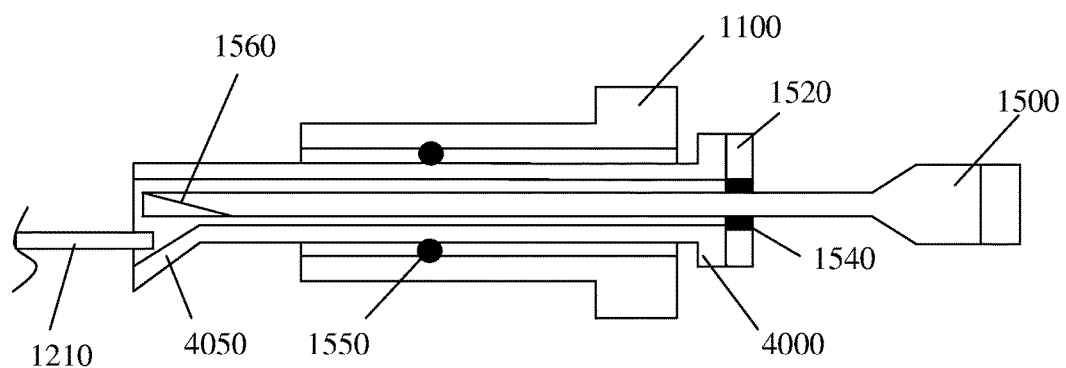
FIGS. 5A-B illustrate two exemplary laparoscopic trocar systems incorporating means for needle capturing, in accordance with exemplary embodiments of the invention.
Figure 5B:
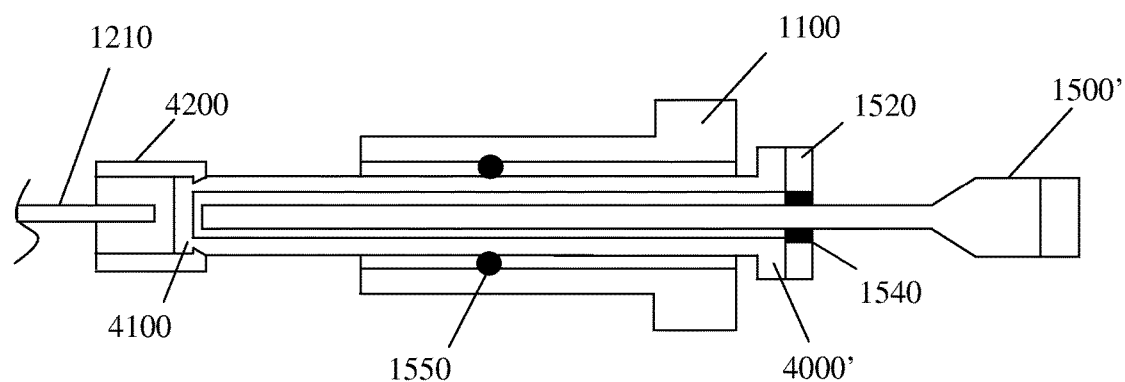

Reference is now made to FIGS. 5A-B which illustrate two exemplary laparoscopic trocar systems incorporating means for needle capturing. In FIG. 5A, a schematic cutaway illustration of an exemplary laparoscopic trocar system is shown in a specific deployment stage, comprising a sheath 1100, an internal sleeve 4000 telescopically engaging with sheath 1100, and an endoscope 1500 telescopically engaging with internal sleeve 4000. In some embodiments, the system is sealed to gas escaping from treated body cavity using valve 1550 maintained between sheath 1100 and internal sleeve 4000 and an optional seal 1540 between internal sleeve 4000 and endoscope 1500. In this exemplary embodiment, internal sleeve 4000 includes an expandable distal end 4050. Optionally, distal end 4050 is expandable from original smaller diameter of sleeve 4000 to a chosen and/or predetermined diameter, either axisymmetric or in a non-cylindrical fashion (as shown in FIG. 5A). Expanding distal end 4050 facilitates an easier approach for capturing a distal end of needle portion 1210 as shown. It is common that a laparoscopic vision system has a vision range that is angled to its longitudinal axis and as shown in this example, endoscope 1500 includes a tapered vision pick-up lens 1560 located at its distal end. In some embodiments, expandable distal end 4050 is substantially transparent to visual pick-up and illumination.

In some embodiments, when needle portion is pushed proximally through internal sleeve 4000 lumen, endoscope 1500 is adequately withdrawn until completely passing through seal 1540, and then needle portion 1210 takes its place and re-seals the trocar system via seal 1540. Alternatively, when needle portion 1210 passes valve 1550, internal sleeve 4000 may then be removed with endoscope 1500, and valve 1550 will close over needle portion 1210 thereby re-sealing the trocar system.

In FIG. 5B a cutaway illustration of a second exemplary laparoscopic trocar system is shown comprising a sheath 1100, a capturing device 4000' telescopically connected in sheath 1100, and an endoscope 1500' telescopically connected in capturing device 4000. In this exemplary embodiment, capturing device includes a separated capturing part 4200 which may be integral (not shown) or detachably connected to capturing device distal end 4100. Capturing part 4200 may be a sleeve with an inner lumen sized for needle portion 1210 introduction (as shown), but may be any other capturing element that may or may not include a grasper, a magnet, a threading, an adhesive, or any other feature. Capturing part 4200 may be disposable while capturing device 4000 may be designed for single or multiple uses. This option may be especially useful if needle portion 1210 is promoted through sheath 1100 in parallel to withdrawing of capturing device 4000. One benefit may be that endoscope 1500 may not be removed from capturing device 4000 (now replacing a guiding cannula) and allow visual surveillance during the entire deployment session. In this option, the sealed distal end 4100, which is preferably transparent, may serve also as a protection barrier between needle portion 1210 and endoscope 1500. Different sealing elements (not all are shown) may be placed between sheath 1100 and capturing device 4000 and between capturing device 4000 and endoscope 1500, either one-way or two-ways seals.

In an exemplary embodiment, a ring 1520 incorporating a sealing core 1540 is introduced between capturing device 4000 and endoscope 1500. Sealing core 1540 may be a pliable rubber-like material with an inner diameter that is slightly smaller than endoscope 1500 outer diameter, and an outer diameter that is greater than capturing device 4000 inner diameter. Ring 1520 may be integral to capturing device endoscope 1500 or integral to capturing device 4000, or alternatively be a separate element optionally connectable to any of the two devices. It may be useful for practical reasons, though not necessary, that sealing core 1540 is a one-way seal which is active once endoscope 1500 is introduced and settled in capturing device but becomes not active once endoscope 1500 is pulled proximally.

Figure 6A:
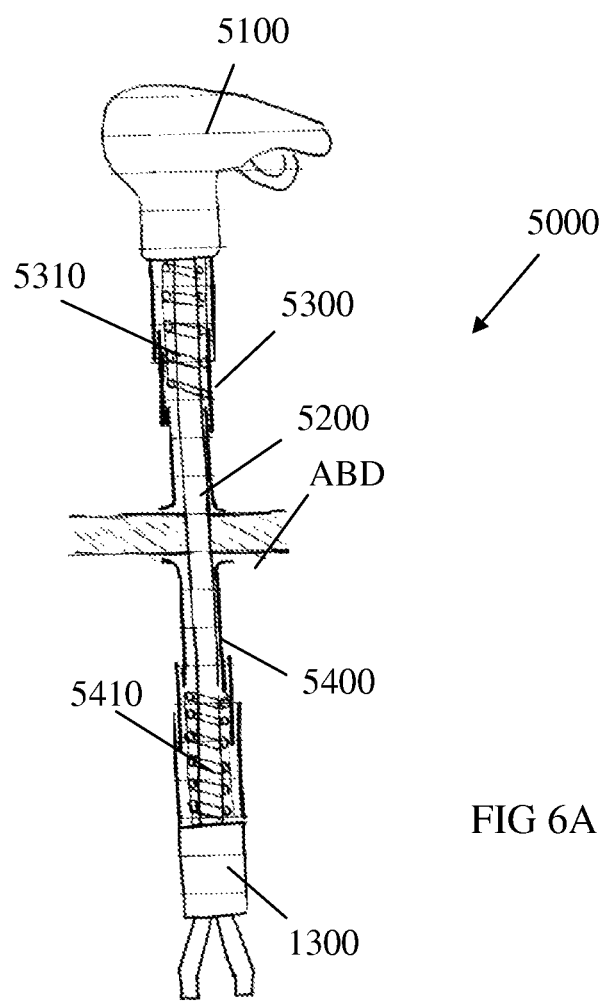
FIG. 6A illustrates an exemplary manipulator system, in accordance with an exemplary embodiment of the invention.

Reference is now made to FIG. 6A showing a cutaway illustration of an exemplary manipulator system 5000 in deployed position after connecting to tool 1300. Manipulator system 5000 comprises a handle unit 5100, a slender shaft 5200 and an outer-body telescopic frame 5300 and an inner-body telescopic frame 5400, connected to proximal and distal ends of shaft 5200 via proximal spring 5310 and distal spring 5410, respectively. Shaft 5200 may have similar or even smaller diameter than previously described needle 1200 and/or may be made less rigid either by materials and/or form, while an improved resistance to bending, arching, shearing and the like is gained by telescopic frames 5300 and 5400. Telescopic frames 5300 and/or 5400 include at least one tubular member, optionally at least two members capable of telescopically nesting and extending one with respect to the other. Springs 5310 and/or 5410 may be used to provide a normally extended position of telescopic frames 5300 and/or 5400, respectively, for example by connecting them in a first end to the proximal (5300)/distal (5400) end of the most proximal tubular member, and in their second end to the proximal (5300)/distal (5400) end of the most distal tubular member of the telescopic frames. The telescopic manner of frames 5300 and 5400 further allows the operator to maneuver shaft 5200 and tool 1300 in an in-and-out movement while not compromising the external supporting of slender shaft 5200. Telescopic frames 5300 and/or 5400 may respectively be integral, detachably connected or ultimately separated to handle 5100 and/or tool 1300. The distal end of most distal tubular member of telescopic frame 5300 and/or the proximal end of most proximal tubular member of telescopic frame 5400 may be enlarged and/or comprise soft material in order to facilitate an improved articulation characteristics which is more controlled and/or safer to abdominal wall portions in-contact. In an optional scenario, the operator first assembles handle 5100, shaft 5200 and proximal telescopic frame 5300 and introduces manipulator system into abdominal cavity ABD. Then tool 1300 connected with distal telescopic frame 5400 are assembled onto the distal end of shaft 5200 via a sheath lumen, as previously described. Tool replacement and/or system disassembly can be achieved in a similar fashion. In some embodiments, only telescopic frame 5300 is used. In some other embodiments, only telescopic frame 5400 is used.

Reference is now made to FIGS. 6B-6D, illustrating isometric views of an exemplary external telescopic needle fortifier unit 5500, in accordance with an exemplary embodiments of the present invention. Fortifier 5500 includes a proximal portion 5520 connectable (e.g., by a thread) to a handle controlling unit (not shown), a telescopic body 5510 and a distal portion 5530. FIG. 6B illustrates a needle portion 1210 connected with a tool 1300 fortified with fortifier 5500. Fortifier body 5510 includes a plurality of elements, such as element 5512*i*, slidably and telescopically connectable one to the other in sequence, so that fortifier body 5510 may be extended to any length from a full compression length L1 and a full extension length L2. Fortifier body 5510 and any of its members may be rigid or semi rigid, optionally made from stainless steel or hard plastic. In some embodiments, length L2 is at least 0.3 times the total effective length of needle portion 1210, optionally at least 0.5, optionally about ⅔ its length. Exemplary lengths of L2 may be within the range 10 to 50 cm, optionally within the range 20-30 cm. In some embodiments, length L1 is at most 0.75 times the length L2, optionally at most 0.5 its length, optionally about ⅓ its length. In some embodiments, at least one of the members, optionally at least two members such as the most proximal and most distal members, includes an inner portion having a length that is connected to or snuggly fitted over a corresponding length portion of needle portion 1210, thereby diminishing buckling of the needle in fortifier 5500. In some embodiments such an inner portion is of component made of soft and/or comprising smooth surfaces to ease sliding with minimal friction.

Fortifier body 5510 may include a spring along at least part of its length for achieving a regularly-extended characteristic. Such characteristic may be beneficial for exerting continuous compressive force towards an external abdomen portion around needle 1210 entry point. Alternatively no spring is used and optionally the fortifier body may be selectively affixed to any length between L1 and L2. In some embodiments, the latter arrangement maintains a continuous sealing and/or contact between distal portion 5530 and by providing adhesive or other affixing means (e.g., a patch) to a contact surface 5532 of distal portion 5530. This way the surgeon may extend or contract the telescopic fortifier 5500 to a chosen length while its distal portion 5530 is maintained affixed to patient's skin. Fortifier 5500 may be locked in any chosen length whereby a chosen length of the needle portion projecting in abdominal cavity is also kept unchanged. If the needle is coupled with grasping means it may be used as a retractor for holding a body organ at a fixed height or position in the body cavity for an entire treatment period. In such cases the fixating means of fortifier 5500 to patient's skin may be designed to resist forces of up to 10 kg, optionally up to 5 kg, optionally up to 3 kg, or higher or lower or intermediate. In some embodiments, distal portion 5530 is disposable and intended for single-use, whereas other parts of fortifier 550 may be disposable or intended for multiple-use.

In some embodiments, especially when visualization is partial or non-aligned with sheath axis, other means may be provided for active grasping and/or aligning of a needle portion in patient's body cavity. Active means may refer to any mechanical, electrical, electro-mechanical, magnetic and/or any other device which may be positioned at a distal end of an external working sheath, a trocar or an internal sleeve, or may be provided as a separate capturing device deliverable into body cavity via any of sheath and internal sleeve lumens. These active means may be manually or robotically operated from outside body cavity. In some embodiments, such active means are provided in a kit further comprising a detachable camera head connectable to a distal needle portion. In some embodiments, visualization is facilitated using a laparoscopic camera detachably connectable to percutaneous needle instead of, or in combination with, a laparoscopic visualization unit provided intraluminally via trocar and/or internal sleeve.

Figure 7A:
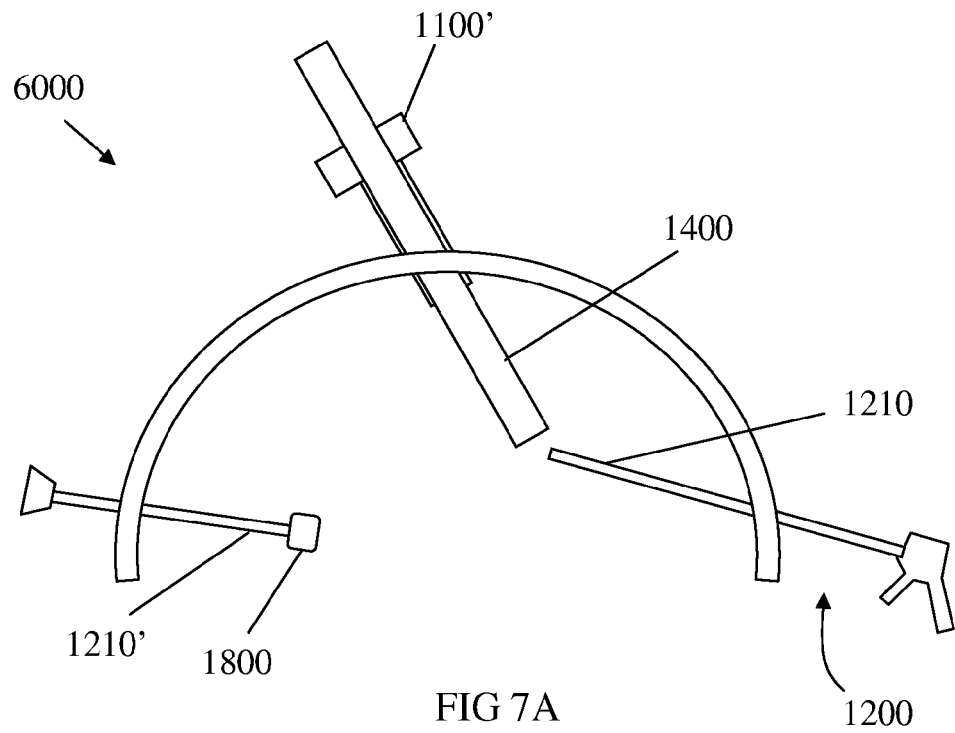
FIGS. 7A-F illustrate different stages needle capturing using a loop type needle capturing device, in accordance with an exemplary embodiment of the invention.
Figure 7B:
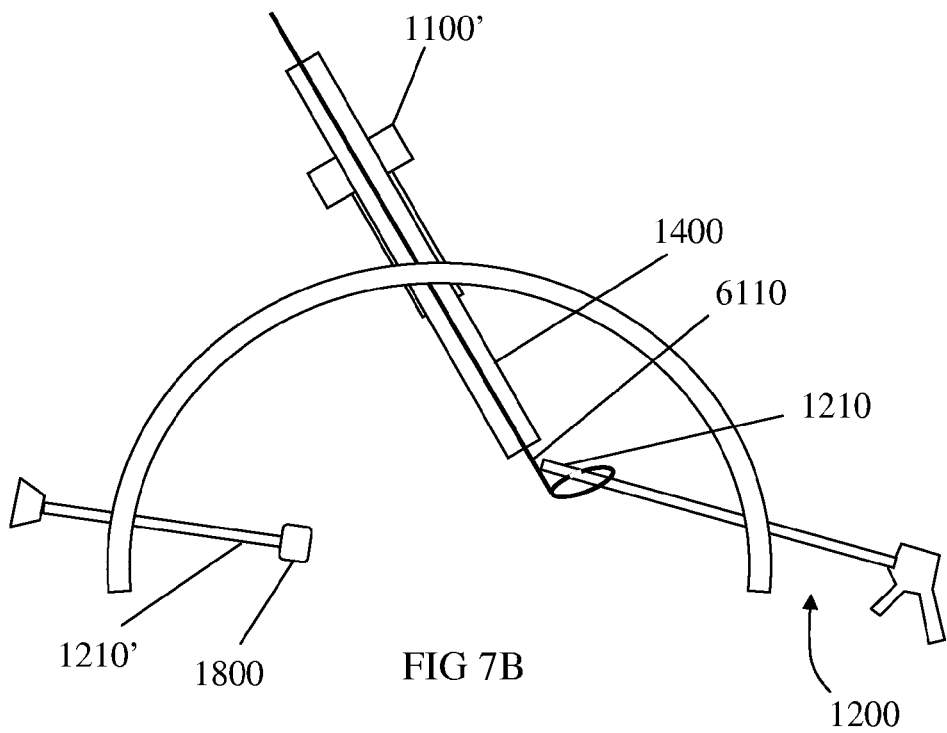

Reference is now made to FIGS. 7A-F, which illustrate different stages of capturing needle portion 1210 using a loop-type needle capturing device 6100, in accordance with an exemplary embodiment of the invention. As shown in FIGS. 7A-B, a laparoscopic surgical system 6000 is provided and deployed for a surgical intervention in a patient's body cavity, the laparoscopic system comprising guiding cannula 1400, telescopically connectable and/or slidable through sheath 1100', needle portion 1210 percutaneously inserted into the body cavity and operable from outside patient's body, and a camera head 1800 detachably connected to a distal portion 1210' of a second percutaneously inserted needle manipulator. Loop-type capturing device 6100 is delivered via guiding cannula 1400 and is maneuvered towards needle portion 1210 in order to capture and grasp it under camera 1800 visualization. Then needle portion 1210 can be pulled out of patient's body through guiding cannula 1400 in order to place a surgical head thereto.

In some embodiments, needle capturing device 6000 comprises an elongated slender body 6110 which is coupled to or ends with a loop 6120. In some embodiments, capturing device 6100 or any of its parts, either body 6110 or loop 6120, is at least partially made from elastic, optionally spring type and/or a super-elastic material, optionally from a shape memory plastic or alloy. Such material may include any of Ni—Ti alloy, Co—Cr alloy, 316L alloy, 17-4 alloy, custom 465 alloy, BioDur™ alloy or any other metal and/or polymeric material.

Figure 7C:
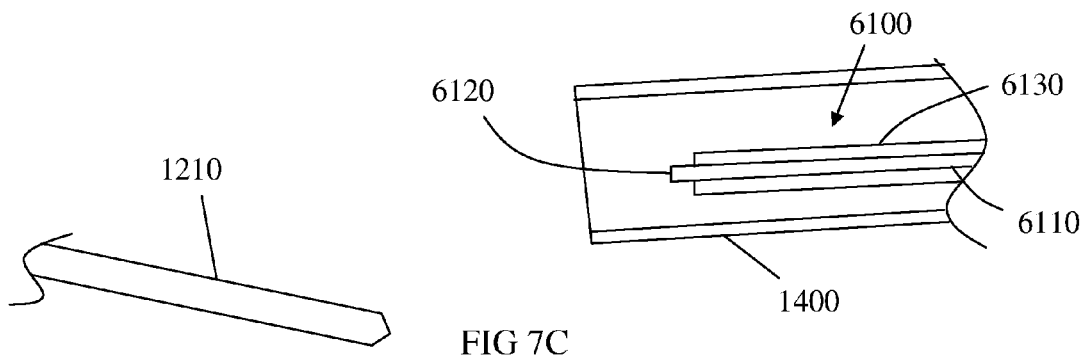
Figure 7D:
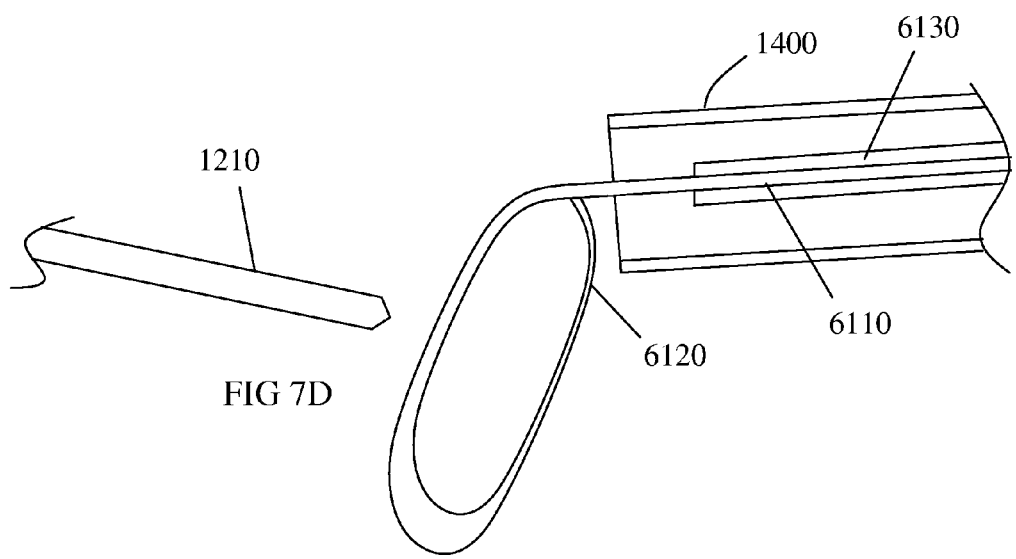
Figure 7E:
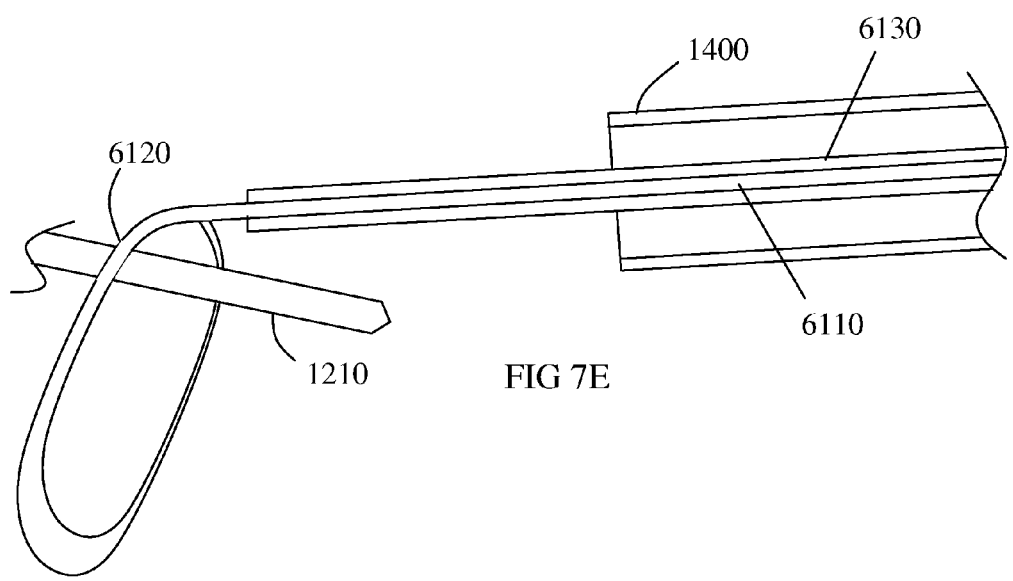

In some embodiments, capturing device 6100 is so configured that in a relaxed state (i.e., when under substantially no external forces or stresses) body 6110 will be shaped in a substantially straight fashion along an elongated axis while loop 6120 is angled with respect to the elongated axis, optionally with its distal end projecting forward as illustrated in FIGS. 7D and 7E. In some embodiments, capturing device 6100 is also configured to deform, optionally elastically (e.g., collapsed and/or substantially straighten) when loop 6120 is located in or forced into lumen of diameter constricting means. In some embodiments, capturing device 6100 further includes an outer tube 6130 which is slidably mountable over body 6110 and loop 6120, causing loop 6120 to extendedly collapse therein when pushed over it (as in FIG. 7C) and allowing loop 6120 to regain an opened loop form when withdrawn (as in FIG. 7D).

FIGS. 7C-F provide a zoom-in stepwise illustration of needle portion 1210 capturing using capturing device 6100. As shown in FIG. 7C, guiding cannula 1400 is approached towards needle portion 1210, under camera 1800 visualization. When adjacent needle portion 1210, capturing device 6100 in a collapsed form is pushed distally through cannula 1400 lumen at least until loop 6120 is fully extending outside outer tube 6130, in a relaxed opened form and angled with respect body 6110, as shown in FIG. 7D.

In some embodiments, capturing device 6100 is then pushed forward and/or maneuvered in any chosen direction until the operator determines that the needle portion 1210 is situated inside the lumen of loop 6200 (as shown in FIG.

Figure 7F:
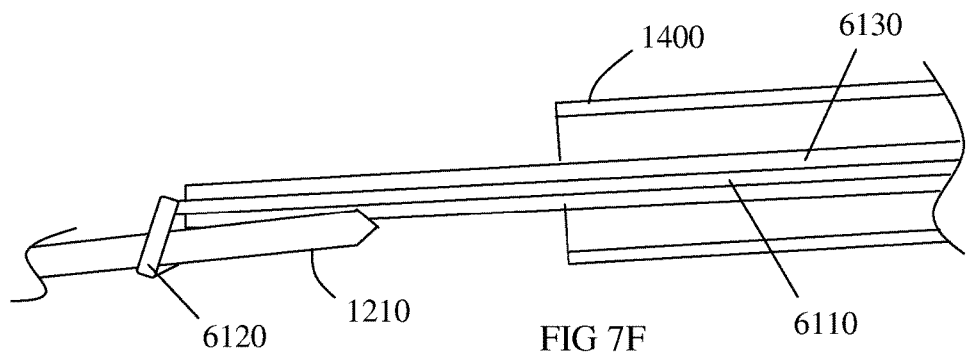

7E). Once needle portion 1210 is encircled by loop 6200, the operator may then push forward outer tube 6130 over body 6110, to re-collapse while fastening its grasp of needle portion 1210 (as shown in FIG. 7F), thereby minimizing an optional undesired release of needle portion 1210.

Figure 8:
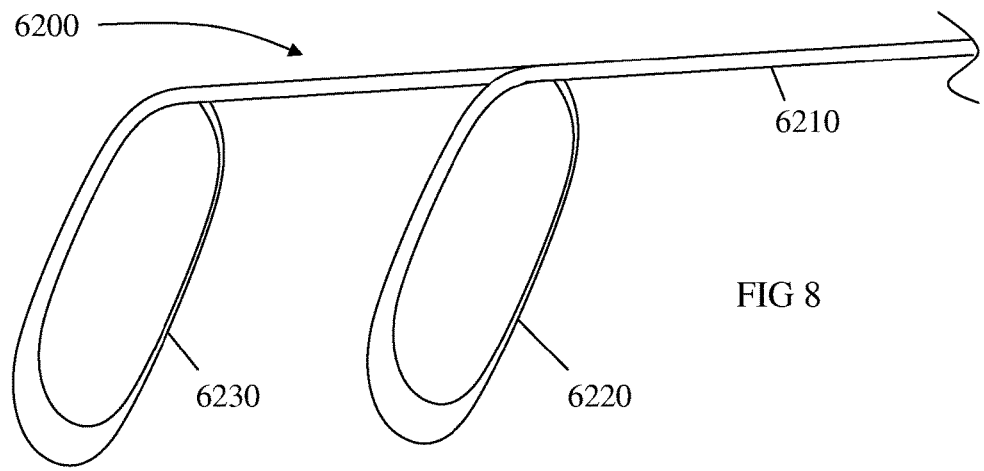
FIG. 8 illustrates an exemplary loop type needle capturing device comprising two loops, in accordance with an exemplary embodiment of the invention.

In order to optionally improve aligning of needle portion 1210, a plurality of loops may be used, as shown in FIG. 8, where another exemplary needle capturing device 6200 includes a distal loop 6230 and a proximal loop 6220 angularly projected along body 6210. Grasping a needle portion at two or distant points along its length will improve or facilitate a predetermined alignment and ease entry to a guiding cannula.

Figure 9:
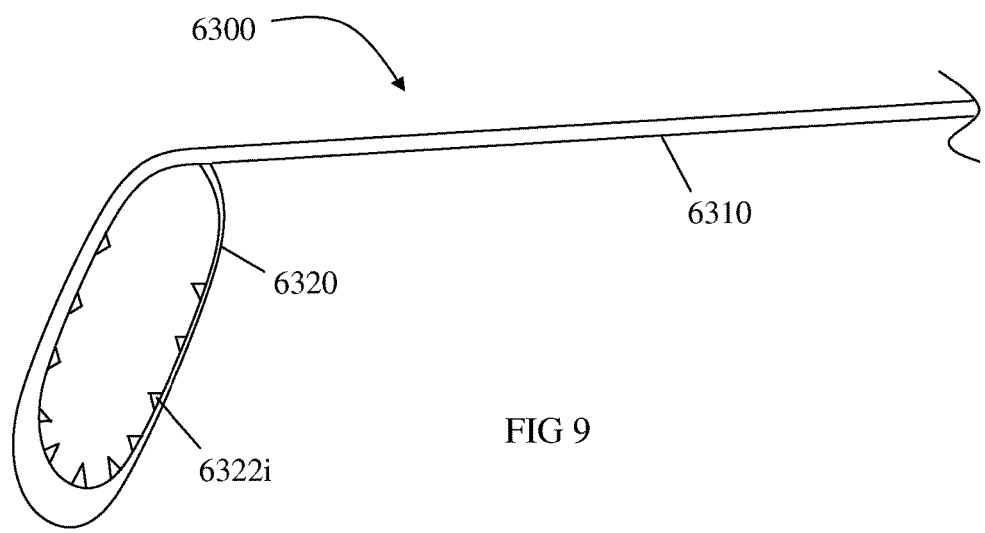
FIG. 9 illustrates an exemplary loop type needle capturing device comprising a teethed loop, in accordance with an exemplary embodiment of the invention.

In some embodiments, other means may be applied to loop type capturing device in order to optionally improve its grasping characteristics of needles. FIG. 9 illustrates another exemplary loop type needle capturing device 6300 which comprises a loop 6320 having a plurality of projections or teeth 6322$i$ (where "i" stands for any number between 1 and a chosen total number of teeth). Teeth 6322$i$ may be made from metal or polymeric materials and may be sharp or blunt. Other possibilities may include using adhesives, magnetic materials, braided or other woven parts or others. Needle portion 1210 itself may include at least one recess or any other alternative means for improve grasping and/or clinging thereto (not shown).

Figure 10A:
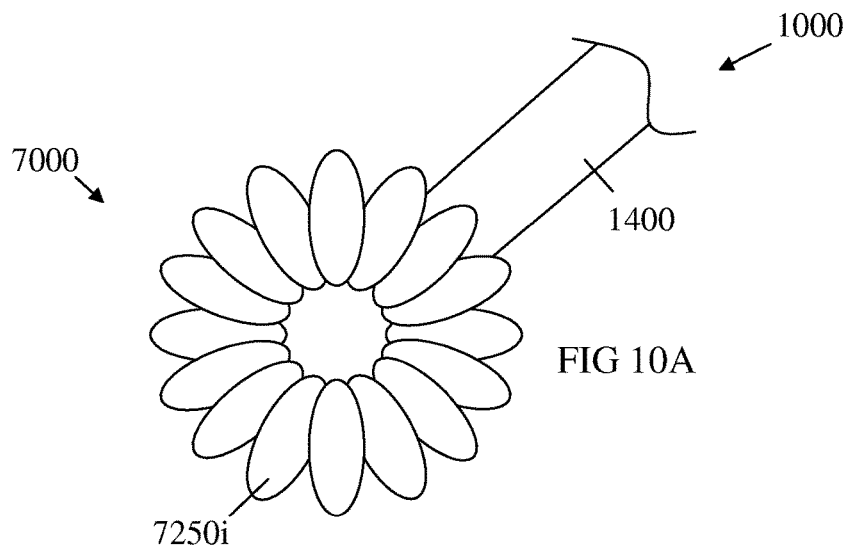
FIGS. 10A-E illustrate exemplary laparoscopic trocar units comprising an expandable funnel type mechanism, in accordance with exemplary embodiments of the invention.
Figure 10B:
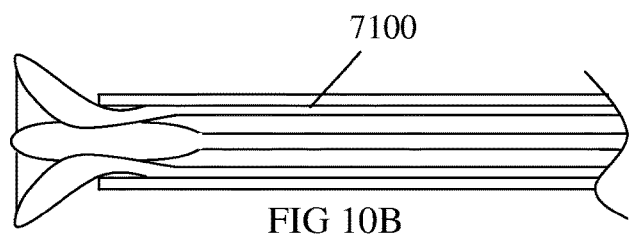

In order to improve ease of capturing and/or slipping a needle portion into guiding cannula 1400 the latter may be adapted to laterally extend at its distal end. Reference is now made to FIGS. 10A-B which illustrate different views of an exemplary laparoscopic trocar unit 1000 incorporating an expandable funnel type mechanism 7000, in accordance with an exemplary embodiment of the invention. In some embodiments, mechanism 7000 includes an elongated body 7100 distally connected to a funnel portion 7200 which includes a plurality of petals-like elements 7250$i$ (where "i" stands for any number between 1 and a chosen total number of petals) that are patterned in a flower-like configuration (as shown in FIG. 10A). In some embodiments, each petal-like element 7250$i$ may be connected to a thin wire, strip or bar, whereby all such elements collectively assembling body 7100. In some embodiments, funnel portion members are substantially rigid and/or hardened thereby avoiding undesired sticking of sharp objects therethrough, such as of a sharp tip of a microlaparoscopic needle, as needle 1200. In some embodiments, mechanism 7000 is elastic at least in part. In some embodiments, mechanism 7000 is adapted to be pushed or pulled through guiding cannula 1400 lumen, in a way that it can be distally projected until fully opening outside cannula 1400 and/or re-collapse into it where it can optionally encircle and grasp a needle portion collected into cannula 1400.

Figure 10C:
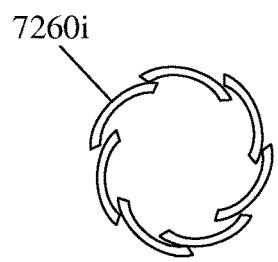
Figure 10D:
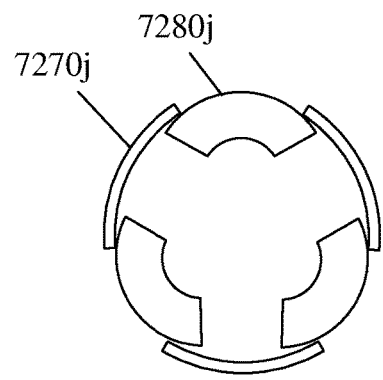

In some embodiments, the expandable funnel type mechanism is also applicable for grasping an end portion of a needle, such as needle portion 1210, either instead or in combination with other active grasping means such as a loop-type grasper. FIGS. 10C-D provide two exemplary embodiments for expandable grasping funnels. FIG. 10C shows a cross section of an expandable funnel having a plurality of petal-like elements 7260$i$ which are organized as an iris diaphragm. FIG. 10D shows a cross section of a different example, where two types of petal-like members are provided, namely outer petals 7270$j$ and outer grasping petals 7280$j$, capable of firmly closing over a needle portion. Petals 7280$j$ are specifically design to be compressed around a needle portion while petals 7270$j$ may be designed and configured to transfer at least part of the force applied by the user to grasping petals 7280$j$.

Figure 10E:
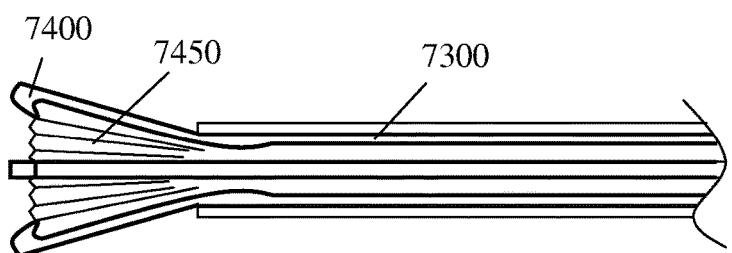

FIG. 10E presents another structural approach for an expandable funnel type mechanism which includes an elongated body 7300 distally connected to a plurality of laterally extendable rods structure 7400. Between each two adjacent rods of rods structure 7400 there provide bellowed panels 7450 that are coupled to and extended in-between the rods and are limitedly extendable and contactable according to relative positioning of the adjacent rods. In some embodiments, bellowed panels 7450 are substantially rigid and/or hard and/or smoothed.

Reference is now made to FIGS. 11A-E illustrating different views of an exemplary laparoscopic system 8000 and members thereof, in accordance with exemplary embodiments of the present invention. Laparoscopic system 8000 includes a needle engager unit 8100 telescopically introduced through a trocar unit 8200. Trocar unit 8200 may be any commercially available laparoscopic port (also known as a laparoscopic cannula), comprising a proximal head 8210 and a distal tube 8220 that optionally ends in a beveled or sharp tip 8230. Head 8210 and/or tube 8220 may include a port seal disposed at its lumen (not shown) which may allow introductions of devices and/or instrumentation therethrough from outside environment to abdominal cavity without damaging its sealing capabilities. Trocar unit 8200 may further include connecting and/or valving means for gas supply to abdominal cavity. Such trocar units may be provided with different lumen sizes, usually of 5.5 mm, 10 mm, 12 mm and 15 mm, although for the ease of description, unless otherwise mentioned, trocar unit 8200 is referred to as having a 12 mm lumen.

Needle engager unit 8100 includes an inner and outer sleeves arrangement, comprising an outer sleeve 8110 slidable over an inner sleeve 8120. Needle engager 8100 is sized and configured to bridge across the port seal of trocar unit 8200 by passing therethrough to thereby deactivate or dismantle the port seal, optionally reversely deactivating it so it can regain its sealing properties once needle engager unit 8100 is removed. Commercially available laparoscopic trocar or port units may include different types of port seal mechanisms, for example an iris-type seal. A port seal mechanism may include at least one collapsible member adapted to maintain a normally extended position but may be forced to at least partially collapse when a laparoscopic device having a smaller diameter distally travels therethrough while maintaining continuous contact with its outer periphery. In such a way, the at least one collapsible member maintain a sealed environment around the laparoscopic device. The needle engager unit 8100 may have an outer dimension configured to travel in trocar unit 8200 lumen up to snugly fitting therein to thereby fully collapsing the at least one collapsible member.

Once stationed in trocar unit 8200, a lumen provided along both ends of inner sleeve 8120 may be used to accommodate travel of a needle distal end from inside patient's body towards outer environment, while preferably allowing sealing, optionally selectively, of its lumen.

Needle engager 8100 has a length large enough to reach any location in the abdominal cavity and/or reach opposite inner wall portions of the abdominal cavity. Outer sleeve 8110 includes an outer tubular body 8112 and a proximal handle 8114, which may be used to push or pull outer tubular body 8112 over inner sleeve 8120. Inner sleeve 8120 includes an inner tubular body 8122 proximally connected or ends with a handle 8126 and distally connected or ends with an expandable funnel 8124. Handle 8126 may be provided completely opened, thereby allowing unhindered gas travel through inner sleeve 8120 lumen, or may be covered with a plug 8128. Plug 8128 may be completely sealed or include a small opening for introducing laparoscopic devices and/or instrumentation of similar or same diameter. Needle engager unit 8100 may be provided with a set of plugs, one of which may be plug 8128, differing with the size of its opening. Exemplary opening sizes may be about 5 mm in diameter for introduction of standard endoscope or tools, about 2 mm in diameter for needle introduction, and a completely sealed plug as mentioned above.

Hence, a guiding cannula according to specific embodiments may be provided in a kit comprising a plurality of plugs differentiated by passive sealing properties and/or opening sizes thereof. Thus, a broad range of differently sized tools or needles is usable with such guiding cannula.

In some embodiments, funnel 8124 is a self-expandable conic structure, expandable from and re-collapsible to a substantially tubular form. At its tubular form, funnel 8124 can be passed at both directions through trocar 8200 lumen with or without outer sleeve 8110. At its expanded conic form, funnel 8124 has a substantially greater span which increase covering area around a needle end and improve capturing probability thereof. Furthermore, the expanded funnel 8124 facilitates a more smoother introduction and accommodation of a nonaligned needle (e.g., projecting at an angle between 100-180° of any coordinate axis with respect to sleeve/trocar longitudinal axis) so that instead of impinging and even penetrating through the funnel, the needle will gently slide over the curved walls of the funnel until aligning with its longitudinal axis.

Funnel 8124 is optionally made from an elastic material so that it can expand and collapse but still maintain minimal rigidity or strength properties to diminish or avoid needle tip penetrating therethrough. Funnel 8124 is preferably made from a pliable material and having, at least partly, elastic and/or plastic portions, optionally facilitating self-expansive characteristics. Exemplary materials may be PVC or polycarbonate having hardness of 70-100 Shore, and it may be manufactured using casting or vacuum forming. The funnel portion may be of various designs and patterns, including a funnel design 8124a (shown in FIG. 11D) having a plurality of petals-like members 10i arranged in a 3D iris diaphragm formation; a funnel design 8124b (shown in FIG. 11E) comprising a conic body 20 having a plurality of oval portions 22i segmented by crimped portions 24i in a manner that ease a controlled and/or a symmetric collapse; and a funnel design 8124c (shown in FIG. 11F) of a fully conic shaped body 30. It may be advantageous to have minimal grooves and slits and that the funnel will be less or non-stretchable to lessen probability of needle stickiness.

By pushing outer tubular body 8112 distally over funnel 8124, the latter will be forced to collapse to a substantially tubular shape having a minimal size, whereas retracting outer tubular body away from the funnel will allow it to regain its expanded size and conic shape. In optional alternative designs, a funnel will expand and/or collapse without the aid of external means such as an outer sleeve, and in some other designs an external covering can be applied only at deployment to trocar 8200, whereas after penetrating into the body the funnel will immediately expand until pulling it through the trocar and out of patient's body. In a compressed mode, funnel 8124 may have a maximal inner diameter equal or less than 10 mm, optionally about 8 mm or about 5 mm, whereas in a fully expanded mode it may have a maximal inner diameter of 50 mm or less, optionally about 30 mm or about 20 mm. When at least partially opened, funnel 8124 may be used to capture a distal end of a needle, such as needle portion 1210 located in a body cavity and/or adjacent an entry point thereto. In some embodiments, needle engager unit 8100 as a whole, or any of its components, is substantially transparent so that the surgeon can immediately notice needle protrusion therethrough, especially when it passes trocar's sealing means.

The following exemplary steps may be taken in sequence or partly in parallel using laparoscopic system 8000 to engage and capture a needle portion in order to equip it with a tool. At first, laparoscopic trocar unit 8200 is introduced and deployed in place (optionally, at the umbilicus), thereby facilitating a selectively opened passage using inner penetratable sealing means (not shown). Gas, usually $CO_2$, may then be compressed into the abdominal cavity until finalized inflation volume is met, and the gas compression means (connected to a dedicated port of the trocar) may be then used to continuously maintain a chosen level of inflation or pressure in view of small portions of gas continuously escaping through natural and/or manmade openings. Needle engager unit 8100 is then passed with its distal end through the lumen of trocar 8200 to protrude into the abdominal cavity. At this stage, funnel 8124 is covered by outer tubular body 8112 forcing it to collapse, while handle 8126 is optionally sealed with a sealed plug. The sealed plug may be replaced (before, during or after deployment in trocar unit 8200) with a plug having an opening sized to accommodate an endoscope, and an endoscope may be optionally positioned in the inner sleeve lumen 8120 to facilitate visualization. Alternatively or additionally, other visualization means may be applied either via inner sleeve 8120 or through a different entry point or a different trocar to abdominal cavity. A needle distal end is then traced using the deployed visualization means, optionally including its entry point to the abdominal cavity. Optionally, the outer sleeve 8110 is then retracted to a position which allows expansion of funnel 8124 to its maximal size or to any other chosen intermediate size. Then the expanded funnel is manipulated towards the needle distal tip, to surround and capture it. This may be done at any point or area in abdominal cavity volume, and at some preferred instances, at and around the needle entry point when funnel 8124 is in contact and may even be pushed towards the corresponding abdominal inner wall portion. In some embodiments, funnel 8124 has non-sharpened edges in order to avoid harm to body tissues in contact. Manipulation is accomplished by altering the entire needle engager unit 8100 or only the inner sleeve 8120 with respect to outer sleeve 8110. The captured needle end may be grasped by collapsing the funnel on it (accomplished by pushing outer tubular body 8112 over it). Alternatively, the needle is first advanced deeply into inner sleeve 8120 lumen (while or after withdrawing the endoscope from same lumen). Then, funnel 8124 may be re-collapsed and the needle engager unit 8100 can be removed leaving the needle protruding through and proximally over the sealing means of trocar unit 8200 (therefore the passage is still maintained sealed after needle engager unit 8100 is removed). A tool may be coupled to the needle distal end and the needle may then be withdrawn back into the abdominal cavity.

Figure 12A:
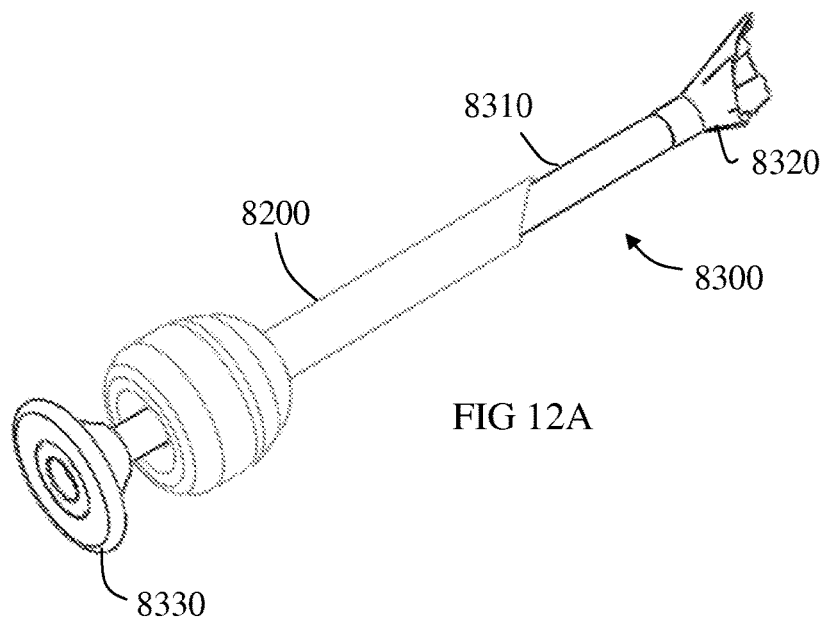
FIGS. 12A-C illustrate different views of an exemplary needle engager unit comprising an asymmetrical expandable funnel component, in accordance with exemplary embodiments of the present invention.
Figure 12B:
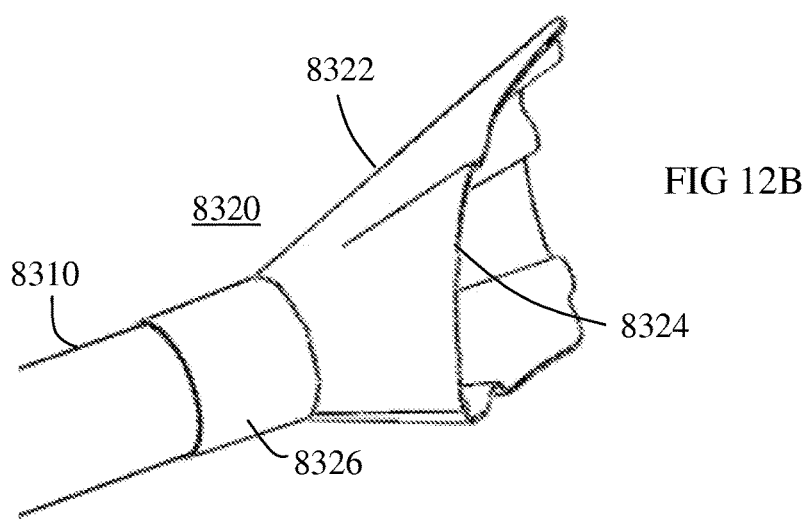
Figure 12C:
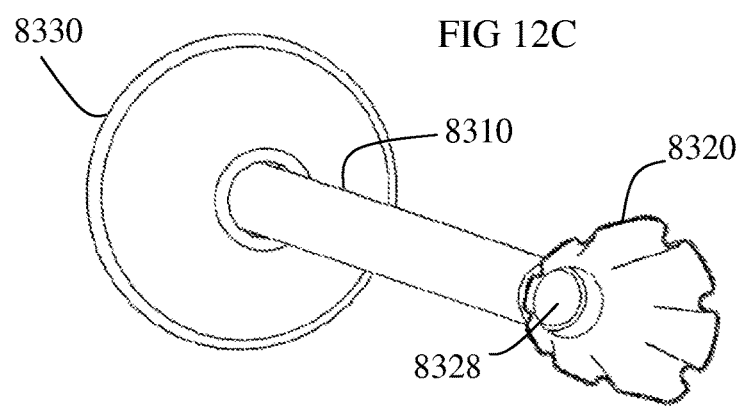

Reference is now made to FIGS. 12A-C which illustrate different views of a needle engager unit 8300 comprising an asymmetrical expandable funnel component 8320, in accordance with exemplary embodiments of the present invention. FIG. 12A shows an isometric view of needle engager unit 8300 when deployed through trocar unit 8200, FIG. 12B shows magnified view of a distal end of needle engager unit 8300 and FIG. 12C shows a shifted front view of the needle engager unit 8300. Needle engager unit 8300 includes an elongated tubular body 8310 distally connected to the asymmetrical funnel 8320 and proximally connected to or ended with a proximal handle 8330. Tubular body 8310 includes a lumen 8328 opened at both ends and extended along its entire length, sized and configured to allow passage therethrough at both directions of a laparoscopic needle with or without a surgical tool connected thereto (not shown). In some embodiments, the asymmetrical funnel component 8320 includes an expandable funnel part 8322 and a distal non-expandable tubular part 8326 used for connecting to or firmly constricting and/or bonded (e.g., glued) over the distal end of elongated tubular body 8310. In some embodiments, the expandable funnel part 8322 is one-sided and includes a tapered edge 8324, and having a first closed side and a second substantially opened side. Such a configuration allows a continuous accurate visualization and monitoring of a needle end entrapment and deployment using an endoscope or a camera projected towards and from the side of funnel part 8322 open end. Such visualization may allow and improved verification abilities of needle entrapment and placement in the funnel 8322 and lumen 8328. Such a design further allows a faster and easier recollapsing of funnel part 8322, and as shown in the figures, it can make redundant the need for an over tube and may collapse when withdrawn back through trocar unit 8200.

Figure 13A:
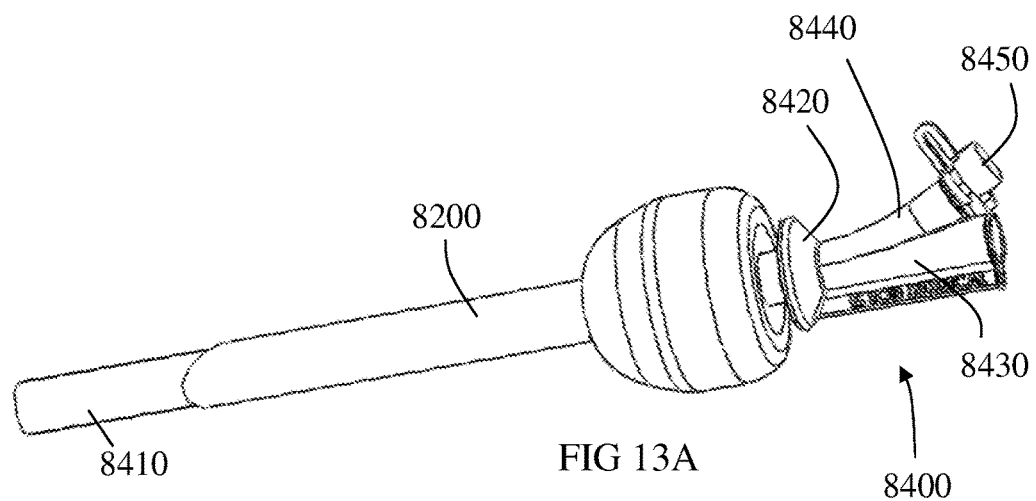
FIGS. 13A-B illustrate elevation view and lateral cut view of an elongated double-lumen introducer, in accordance with an exemplary embodiment of the present invention.
Figure 13B:
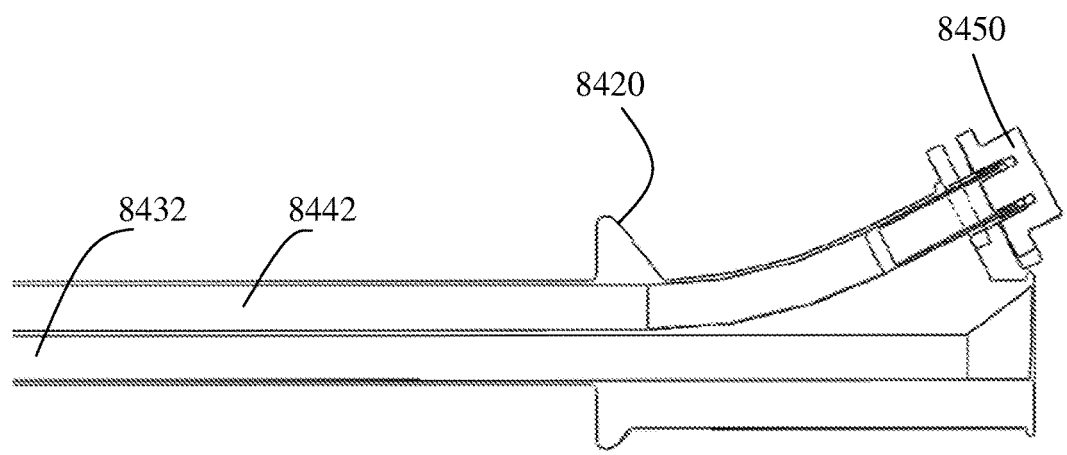

In some circumstances it may be advantageous to use an elongated introducer, readily traversable through the trocar lumen, having more than one port and lumen extending along its length. One advantage may be the possibility to provide different components in parallel while avoiding its potential interaction and/or to provide separate sliding tracks for each one. The small proportions of such an elongated introducer (having external diameter that for example is equal or slightly over 12 mm) have substantial influence to the design and/or flex properties of the elongated introducer and/or the components prescribed to pass therethrough. Reference is made to FIGS. 13A-B which illustrate elevation view and lateral cut view, respectively, of an elongated double-lumen introducer 8400 applicable for introducing end portions of an endoscope and a suction tube (not shown), in accordance with an exemplary embodiment of the present invention. The proposed arrangement allows use of suction according to need without having to first withdraw the endoscope from trocar lumen or to insert the suction tube through a second trocar. Furthermore, the suction tube may be used to clean endoscope or other visualization means, or a lens thereof, by first injecting a fluid (e.g., saline) thereto and then suctioning the fluid using the suction apparatus. Providing suction in parallel to an endoscope is also useful as it saves much time used to aim and use the suction. In FIG. 13A elongated introducer 8400 is shown deployed in standard trocar 8200. Elongated introducer includes a tubular body 8410 which end with a proximal head 8420 optionally having radially extending margins to limit sliding movement in trocar 8200 lumen. Proximally extending from head 8420 are endoscope extension 8430 and suction tube extension 8440. In some embodiments, and as shown in the figures, endoscope extension 8430 is straight and concentric with its corresponding endoscope lumen 8432 whereas suction tube 8440 is curved with respect to its corresponding suction tube lumen 8442. This design is applicable for introduction of a standard rigid endoscope and a flexible or semi-rigid suction tube. Alternative designs are also applicable. In some embodiments, suction tube extension 8440 may be selectively closed with a suction extension plug 8450, as may occasionally happen between non-suctioning intervals where the suction tube is withdrawn. In some embodiments, the elongated introducer is substantially rigid and covering a length adjacent endoscope protrusion length, so that the flexible suction tube may not be uncontrollably loose in the abdomen cavity and be maintained in-place and almost totally surrounded in lumen 8442. The insertion in-parallel of the endoscope and the suction to elongated introducer 8400 is set in a specific angle taken from a range of angles that allow manipulation of the suction with one hand and manipulation of the endoscope with the other hand without interference and clashing between them. Preferably, the presence of properly sized endoscope and suction tube at their corresponding lumens may lessen any gas escape therefrom so that theses lumens may be considered air-tight or sealed according to definitions of the present invention.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A guiding cannula comprising:
an inner sleeve having a proximal end and a distal end;
an outer sleeve slidably receiving the inner sleeve;
a lumen extending axially between a distal opening and a proximal opening, wherein the lumen is configured to receive a laparoscopic device from the distal opening and/or the proximal opening;
a sealing member configured to seal the lumen, wherein the sealing member is fixed relative to the outer sleeve, and the inner sleeve is movable relative to the sealing member;
a handle fixed to the proximal end of the inner sleeve; and
a conic body connected to the distal end of the inner sleeve, wherein the conic body defines an edge along a single plane for guiding the laparoscopic device into the lumen, and the edge is continuous in a contracted configuration and an extended configuration,
wherein the outer sleeve defines an outer diameter adapted to fit in a port lumen of a laparoscopic port having a port seal, said guiding cannula is configured to reversely deactivate said port seal when introduced through the laparoscopic port, said guiding cannula is telescopically extendible to receive the laparoscopic device in said laparoscopic port, and said sealing member is configured to receive said laparoscopic device while sealing said lumen from an outside environment.

2. The guiding cannula according to claim 1, wherein said sealing member is positioned in said lumen.

3. The guiding cannula according to claim 2, wherein said sealing member is configured to seal the lumen in a direction from said distal opening to said proximal opening.

4. The guiding cannula of claim 2, wherein said sealing member comprises a plug adapted to snugly fit in a proximal entry of said lumen.

5. The guiding cannula according to claim 4, wherein said plug is sealed or includes an opening sized to fit said laparoscopic device.

6. The guiding cannula according to claim 1, wherein said edge is actuated between the contracted configuration and the extended configuration by an actuating means.

7. The guiding cannula according to claim 1, wherein said edge is self-expandable.

8. The guiding cannula according to claim 1, wherein said contracted configuration of the edge is a cylindrical shape.

9. The guiding cannula according to claim 1, wherein said sealing member is a two-way valve.

10. The guiding cannula according to claim 1, wherein the outer sleeve defines a sharp needle tip.

11. The guiding cannula according to claim 1, wherein the sealing member covers an opening in the handle to seal the lumen.

12. The guiding cannula according to claim 1, wherein said conic body is made of an elastic material with a hardness of 70-100 Shore.

13. The guiding cannula according to claim 1, wherein the conic body has crimped portions in the extended configuration to ease a controlled and/or symmetric collapse.

14. The guiding cannula according to claim 1, wherein the conic body includes a surface having a continuous conic shape in the extended configuration.

15. The guiding cannula according to claim 1, the sealing member has an opening configured to conform the laparoscopic device to seal the lumen and minimize or completely avoid gas migration through the laparoscopic port and/or the guiding cannula.

16. A guiding cannula comprising:
an inner sleeve having a proximal end and a distal end;
an outer sleeve slidably receiving the inner sleeve;
a lumen extending axially between a distal opening and a proximal opening, wherein the lumen is configured to receive a laparoscopic device from the distal opening and/or the proximal opening;
a sealing member configured to seal the lumen, wherein the sealing member is fixed relative to the outer sleeve, and the inner sleeve is movable relative to the sealing member;
a handle fixed to the proximal end of the inner sleeve; and
a conic body connected to the distal end of the inner sleeve, wherein the conic body includes an edge and a surface adjacent to the edge, the edge extends along a single plane for guiding the laparoscopic device into the lumen and has a contracted configuration and an extended configuration, and the surface has a continuous conic shape in the extended configuration,
wherein the outer sleeve defines an outer diameter adapted to fit in a port lumen of a laparoscopic port having a port seal, the guiding cannula is configured to reversely deactivate the port seal when introduced through the laparoscopic port, the guiding cannula is telescopically extendible to receive the laparoscopic device in the laparoscopic port, and the sealing member is configured to receive the laparoscopic device while sealing the lumen from an outside environment.

17. The guiding cannula according to claim 16, wherein said conic body is made of an elastic material with a hardness of 70-100 Shore.

18. The guiding cannula according to claim 16, the sealing member has an opening configured to conform the laparoscopic device to seal the lumen and minimize or completely avoid gas migration through the laparoscopic port and/or the guiding cannula.

19. A laparoscopic system comprising:
a laparoscopic port having a port lumen and a port seal; and
a guiding cannula having:
an inner sleeve having a proximal end and a distal end;
an outer sleeve slidably receiving the inner sleeve;
a cannula lumen extending axially between a distal opening and a proximal opening, wherein the cannula lumen is configured to receive a laparoscopic device from the distal opening and/or the proximal opening;
a sealing member configured to seal the cannula lumen, wherein the sealing member is fixed relative to the outer sleeve, and the inner sleeve is movable relative to the sealing member;
a handle fixed to the proximal end of the inner sleeve; and
a conic body connected to the distal end of the inner sleeve, wherein the conic body defines an edge along a single plane for guiding the laparoscopic device into the cannula lumen, and the edge is continuous in a contracted configuration and an extended configuration,
wherein the outer sleeve defines an outer diameter adapted to fit in the port lumen of the laparoscopic port, the guiding cannula is configured to reversely deactivate the port seal when introduced through the laparoscopic port, the guiding cannula is telescopically extendible to receive the laparoscopic device in the laparoscopic port, and the sealing member is configured to receive the laparoscopic device while sealing the cannula lumen from an outside environment.

\* \* \* \* \*